US 6,471,650 B2

(12) United States Patent
Powers et al.

(10) Patent No.: US 6,471,650 B2
(45) Date of Patent: Oct. 29, 2002

(54) THREE DIMENSIONAL ULTRASONIC DIAGNOSTIC IMAGING WITH HIGH DENSITY HEXAGONAL ACQUISITION

(75) Inventors: Jeffry E. Powers, Bainbridge Is, WA (US); Michalakis Averkiou, Kirkland, WA (US); Matthew Bruce, Seattle, WA (US); Danny M. Skyba, Bothell, WA (US); Robert R. Entrekin, Kirkland, WA (US); John D. Fraser, Woodinville, WA (US); Clifford R. Cooley, Seattle, WA (US); Brent Stephen Robinson, Kirkland, WA (US); David N. Roundhill, Bothell, WA (US); Gary Allen Schwartz, Seattle, WA (US); Patrick René Pesque, Scottsdale, AZ (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 31 days.

(21) Appl. No.: 09/919,681

(22) Filed: Jul. 31, 2001

(65) Prior Publication Data

US 2002/0045827 A1 Apr. 18, 2002

Related U.S. Application Data

(62) Division of application No. 09/645,872, filed on Aug. 24, 2000.

(51) Int. Cl.$^7$ .................................................. A61B 8/00
(52) U.S. Cl. ....................................... 600/447; 128/916
(58) Field of Search ................................ 600/437, 443, 600/447, 459; 128/916; 73/625–626

(56) References Cited

U.S. PATENT DOCUMENTS

| 5,164,920 | A | * | 11/1992 | Bast et al. ................ 367/140 |
| 5,318,033 | A |   | 6/1994  | Savord |
| 5,623,928 | A |   | 4/1997  | Wright et al. |
| 5,667,373 | A | * | 9/1997  | Wright et al. ............... 600/443 |
| 5,893,832 | A | * | 4/1999  | Song .......................... 600/443 |
| 5,940,123 | A | * | 8/1999  | Daigle et al. ............... 348/163 |
| 5,997,479 | A |   | 12/1999 | Savord et a. |
| 6,066,096 | A | * | 5/2000  | Smith et al. ................ 600/439 |
| 6,299,580 | B1 | * | 10/2001 | Asafusa et al. ............. 600/459 |
| 6,374,674 | B1 | * | 4/2002  | Mine ........................... 73/606 |

OTHER PUBLICATIONS

Fatemi, M. et al., "Application of Hexgonal Arrays in Generation and STeering of Limited Diffraction Beams," IEEE 1994 Ultrasonic Symposium, vol. 16 No. 1, Jan. 1994, pp. 1531–1534.

Fatemi, M. et al., "Efficient Generation of Limited Diffraction Beams by Hexagonal Arrays," Ultrasonic Imaging, vol. 16, No. 1, Jan. 1994, p. 53.

* cited by examiner

*Primary Examiner*—Francis J. Jaworski
(74) *Attorney, Agent, or Firm*—W. Brinton Yorks, Jr.

(57) ABSTRACT

An ultrasonic imaging method and apparatus are described for imaging the coronary arteries of the heart. The vascular system is infused with an ultrasonic contrast agent. A volumetric region of the heart wall including a coronary artery is three dimensionally scanned. A projection image of the volumetric region is produced from the scanning, providing a two dimensional contrast image of the coronary artery with the appearance of an angiogram. Preferably the coronary artery signals are segmented from contrast signals emanating from the myocardium and the heart blood pool so that the coronary arteries are clearly highlighted and distinct in the ultrasonic angiogram.

20 Claims, 16 Drawing Sheets

FIG. 3
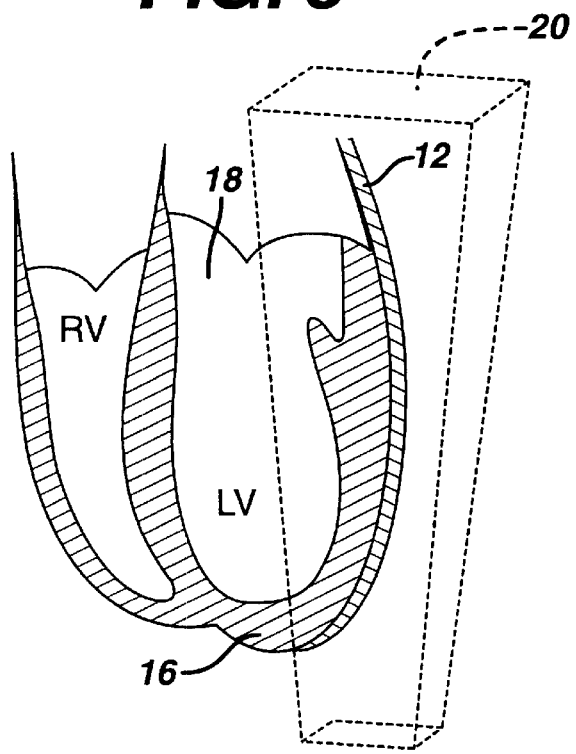
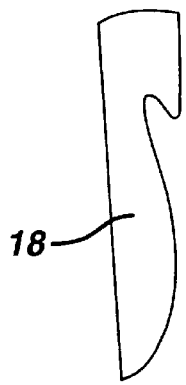
FIG. 4a
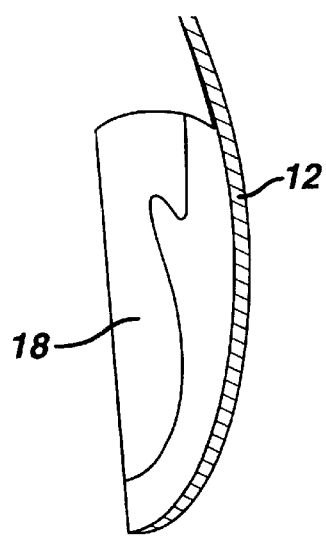
FIG. 4b
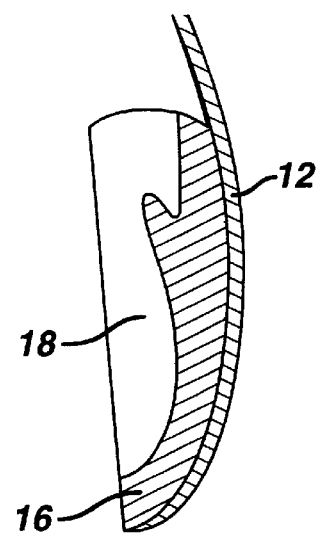
FIG. 4c

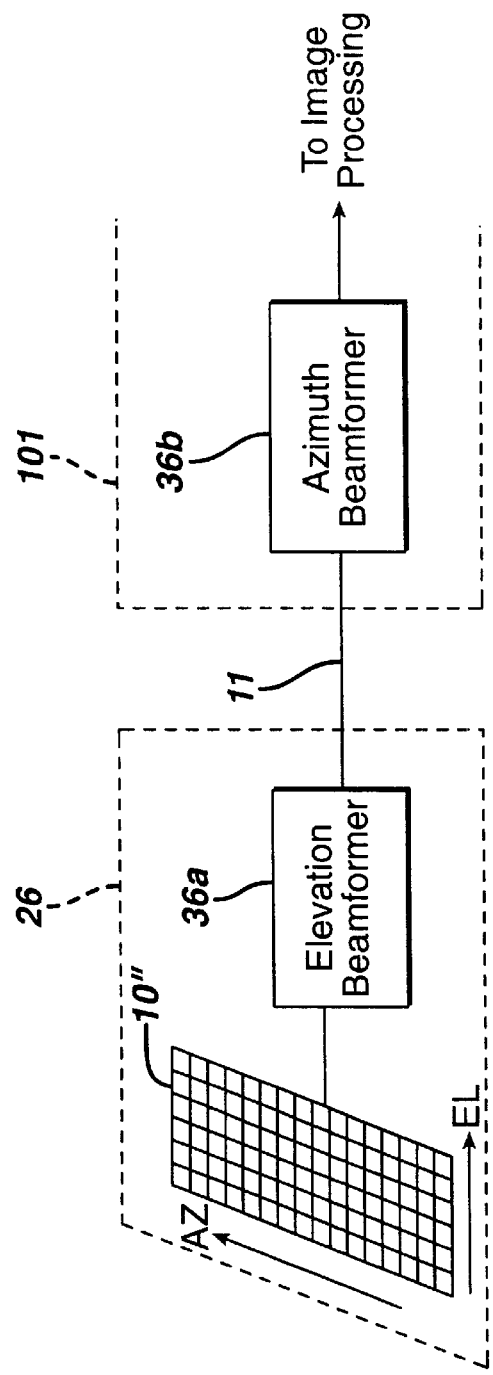
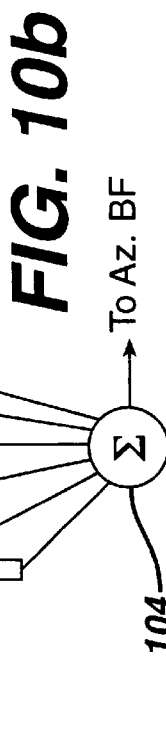
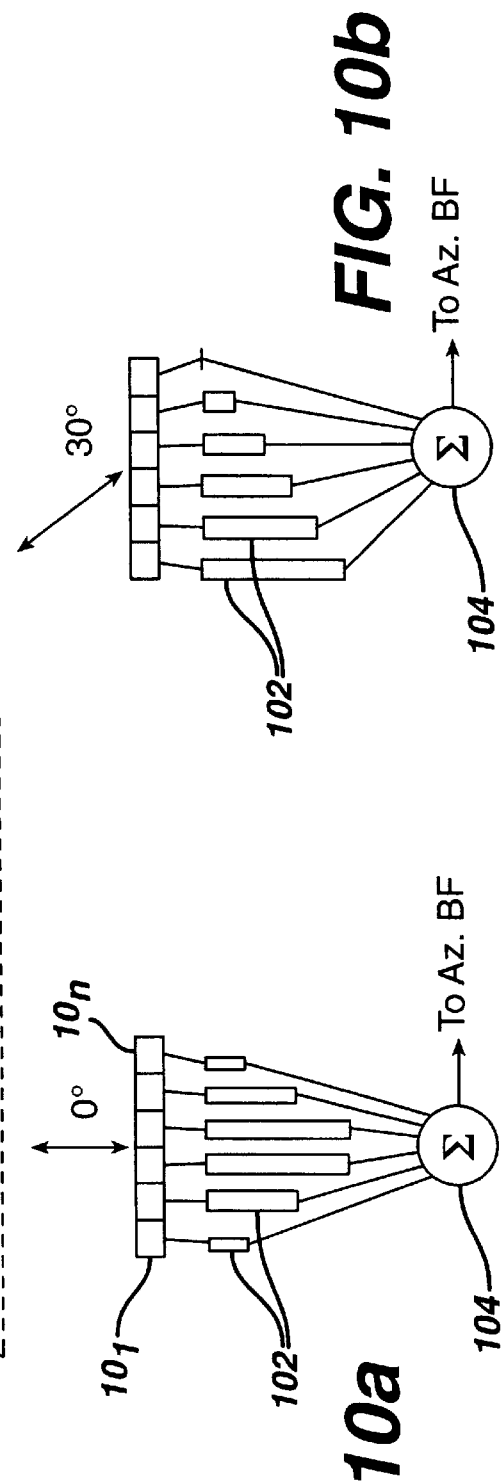
FIG. 9
FIG. 10a
FIG. 10b

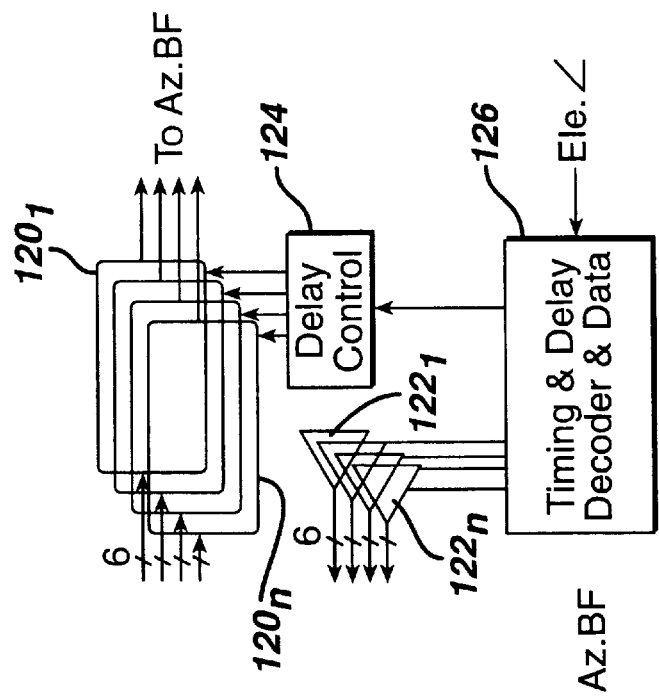
FIG. 12
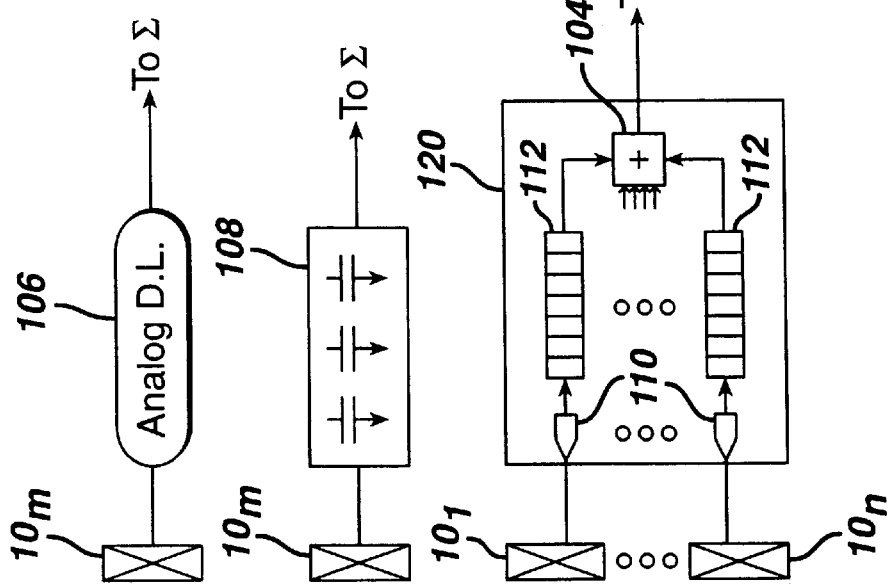
FIG. 11a
FIG. 11b
FIG. 11c

THREE DIMENSIONAL ULTRASONIC DIAGNOSTIC IMAGING WITH HIGH DENSITY HEXAGONAL ACQUISITION

This is a divisional application of U.S. patent application Ser. No. 09/645,872, filed Aug. 24, 2000 and entitled "ULTRASONIC DIAGNOSTIC IMAGING OF THE CORONARY ARTERIES."

This invention relates to ultrasonic diagnostic imaging systems and, in particular, to the use of ultrasonic diagnostic imaging systems to image the coronary arteries.

Early detection of coronary artery disease is important for the treatment and prevention of myocardial infarction, the primary cause of death of adults in the world. One of the principal methods of detection of coronary artery disease at present is the diagnostic angiogram. An angiogram is acquired by injecting a radiopaque dye into the vascular system, usually by means of a catheter. The radiopaque dye infuses the coronary arteries, and a radiological projection is made of the infused arteries onto a radiographic sensor. The resultant angiogram will reveal the lumens of the arterial vessels of the heart as the radiopaque dye flows through them. A narrowing of the infused lumen will provide an indication of an obstruction of a vessel and a potential condition for infarction.

Ultrasound has been considered as a possible modality to use for coronary artery examinations, which would have the advantage of eliminating the exposure of the patient to the radiation used to form the angiogram, to radiopaque dyes, and the surgical catheterization procedure. However, ultrasonic imaging has its own limitations. One is that the major coronary arteries are located on the irregularly curved surface of the heart and traverse tortuously along the epicardial surface of the heart. Thus, the coronary arteries cannot be viewed in a single image plane, the most prevalent way ultrasonic imaging is done. Furthermore, imaging of the coronary arteries is impeded by the rib cage, which largely blocks ultrasound, and by the motion of the heart itself. Thus, even when a portion of the coronary arteries is accessible to ultrasound, the images of the coronaries are likely to be fleeting, blurred, and of relatively poor resolution.

In accordance with the principles of the present invention, a technique and apparatus are provided for ultrasonically imaging the coronary arteries. The technique includes the use of an ultrasonic contrast agent to sharply reveal the coronary arteries against their background of the myocardium and the lungs, even when the heart is in motion. The apparatus includes a three dimensional ultrasonic imaging system which is capable of scanning a three dimensional volume which includes at least a portion of the coronary arteries. In one display format the three dimensional volume including a coronary artery is projected onto a display plane to produce an ultrasonic image in the same manner as an angiogram. In another display format the three dimensional volume is displayed together with a realtime two dimensional image of a plane of the three dimensional volume. In another display format the bloodflow path of a coronary artery is displayed in a separate, "straightened" rendering of the vessel.

Conventional radiological arteriograms only detect a few branches down the arterial tree from the major coronary trunks. Ultrasound is capable of also visualizing transmural arteries. Thus, the present invention has the potential of providing visualization of vessels not seen with conventional angiography.

In the drawings:

FIG. 3 illustrates a three dimensional volume intersecting a portion of the wall and chamber of a heart;

FIGS. 4a–4c illustrate the sequential infusion of the chamber, myocardium and coronary arteries of the portion of the heart inside the volume of FIG. 3;

FIG. 9 illustrates the partitioning of beamforming between a scanhead and an ultrasound system;

FIGS. 10a and 10b illustrate the steering of a beam in the elevation direction by a scanhead beamformer;

FIGS. 11a, 11b and 11c illustrate different embodiments of a scanhead elevation beamformer;

FIG. 12 illustrates the organization and control of a number of beamformer channels of a scanhead elevation beamformer;

Figure 1:
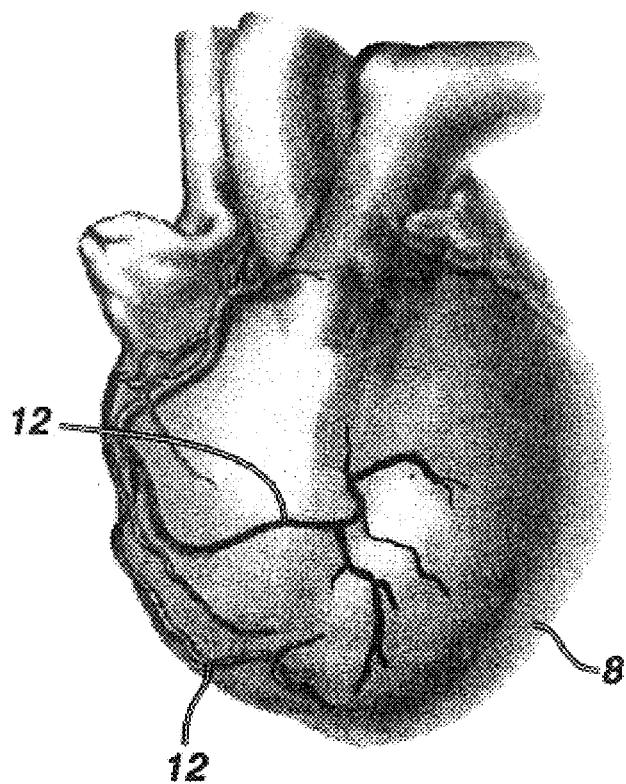
FIG. 1 illustrates coronary arteries traversing the surface of a heart.

Referring first to FIG. 1, a picture of a heart 10 is shown. Located on the outer surface of the heart are the coronary arteries 12, which provide a continuous supply of blood to the heart muscle, the myocardium. The outer surface of the heart is irregularly rounded with periodic depressions and elevations, and the coronary arteries. located on this surface follows this continuously bending surface and its high and low points. Thus, the coronary arteries are not located on a planar surface, but on a surface which undergoes many curves and contortions. The coronary arteries cannot be imaged by a single plane which bisects the heart, but by techniques which will image the three dimensional paths of the coronary arteries and all of their bends, twists, and turns.

Figure 2:
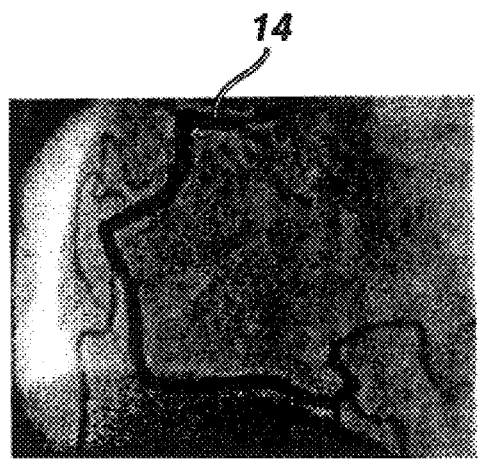
FIG. 2 illustrates an angiogram of a portion of the coronary arteries shown in FIG. 1.

FIG. 2 depicts an angiogram of the coronary arteries of the heart of FIG. 1. The angiogram of FIG. 2 is formed by first injecting a radiopaque dye into the body which infuses the coronary arteries. A broad beam of x-rays is then transmitted through the chest of the patient and onto a radiographic plate on the opposite side of the patient. The radiographic plate is continually scanned to create an image. The x-rays which pass through the heart without intersecting the coronary arteries will appear as bright areas in the image, but x-rays which strike a dye-infused artery will not reach the radiographic plate, leaving an x-ray "shadow" 14 of the coronary arteries on the plate. The resulting shadow image of the coronary arteries will appear as shown in FIG. 2. Since a large area or even the full heart is illuminated with x-rays, the twisting and turning coronary arteries on the heart surface will leave a pattern in the transmitted x-rays, even though their twists and turns extend in three dimensions. Obstructions in the coronary arteries will be revealed by sudden changes in the width and/or brightness of an arterial "shadow."

FIG. 3 depicts the ventricular region of a heart. The left ventricle LV and right ventricle RV are depicted on the drawing. A portion of the heart wall and left ventricle are to be imaged in this example, and are contained within an imaging volume 20. The chamber volume of the left ventricle is indicated at 18, the myocardium is indicated at 16, and the coronary arteries 12 are located on the outer surface of the myocardium. An ultrasonic contrast agent is introduced into the body of the patient and the imaging volume is scanned ultrasonically for both the harmonic and the nonlinear fundamental return from the contrast agent. Initially, before any of the contrast agent has reached the heart, there will be no harmonic return except that caused by nonlinear propagation of the ultrasonic signal, which will be relatively low in intensity. This tissue harmonic return can be reduced by pre-distorting the transmitted pulse as described in U.S. Pat. No. 5,980,457 or by thresholding or other techniques. When the contrast agent reaches the heart through the circulatory system it will initially fill the chamber of the left ventricle in the imaging volume 20, as depicted in FIG. 4a. The left ventricle will light up with a strong harmonic return and will appear brightly in the ultrasonic image. As the contrast agent is pumped from the heart it will next infuse the coronary arteries 12, as depicted in FIG. 4b. At this stage both the heart chamber 18 and the coronary arteries 12 will appear brightly in the ultrasonic image. Finally the contrast agent will perfuse the capillary bed of the myocardium 16 from the coronary arteries 12. The three regions 12, 16 and 18 will then appear brightly illuminated by the contrast agent return echoes as depicted in FIG. 4c.

Since the purpose of the procedure is to examine the coronary arteries with as little clutter from other tissue as possible, it is the second stage of infusion, that depicted in FIG. 4b, which is of primary interest. Hence the clinician should be recording the sequence of events so as to capture the ultrasonic images when the coronary arteries are infused with contrast agent and before the myocardium becomes perfused, since harmonic signals from the myocardium are unwanted and would be regarded as clutter. The harmonic return from the LV chamber is also considered clutter as it is unwanted harmonic signals and can interfere with the projection of the infused coronary arteries onto an image plane. When images such as those depicted in FIG. 4b have been captured, they are preferably processed to eliminate the unwanted signal from the heart chamber 18. This can be done by adaptive beamforming and/or by image post-processing which spatially mask out the unwanted image signals. Since the left ventricle 18 is infused first, an algorithm which detects the initial harmonic return and then masks out image areas contiguous with the initial harmonic return within one or two heart cycles can effectively remove heart chamber signals from the image. Another technique for masking the left ventricular return is to recognize that the left ventricle is a large blood pool and eliminate displaying signals in large area which lack tissue return signals. Thresholding can be used to segment between blood pool signals which have a blood signal density of 100% and the approximately 6% blood signal density of tissue. Another sensing technique is to operate in the fundamental frequency spectrum and recognize that fundamental frequency signals returned from blood are of a lower amplitude than echoes returned from tissue. Harmonic signals returned from areas with predominately low amplitude fundamental signal returns are eliminated from the display to mask the left ventricle. Yet another technique is to recognize that blood-flow velocity in the left ventricle is greater than that in the coronary arteries or myocardium, and mask out the highest velocity signals from the display. The remaining bright image signals from the coronary arteries can then be displayed in a three dimensional display, or projected onto a darkened image plane as by three dimensional maximum intensity rendering to produce a two dimensional ultrasonic projection image of the coronary arteries which will appear much like an angiogram and hence can be used for diagnosis by clinicians familiar with angiograms.

The segmentation of image areas into blood and myocardium can also be used to adaptively beamform in order to increase spatial resolution and temporal resolution in the myocardium. Such a process would generally use larger transmit apertures (with less beam width but requiring more transmit cycles) in the regions of interest (e.g., the myocardium). Smaller transmit apertures are used in the blood pool regions to permit higher-order multiline, and thereby provide faster acquisition. In addition to these aperture adaptations, adaptive beamforming techniques which enhance the imaging of the coronary arteries include sensing the intensity of received signals so as to detect the high intensity return signals from the contrast agent infused blood pool of the left ventricle, and responding by reducing transmit power to the left ventricle, since the left ventricle signals are unwanted and reduced transmit power will cause less disruption of the agent in the left ventricle which is being pumped to the coronary arteries. Another alternative. when using multiline reception, which requires a "fat" (broad) beam to insonify multiple scanlines simultaneously, is to adaptively alter the aperture and hence narrow the transmit beam profile when overlapping the left ventricle, since the beam need only be broad enough to insonify the coronary arteries and not the coronary arteries and the left ventricle. Yet another adaptation is to optimize time-of-flight adjustments for tissue and not blood, and to inhibit these adjustments when receiving blood pool signals from the left ventricle, which is not the target of interest. Yet a further adaptation is to adaptively tailor the aperture in consideration of. transducer elements which are blocked by the ribs when imaging the heart transthoracically.

It has been found that the coronary imaging procedure can be conducted to prevent the third stage shown in FIG. 4c from effectively occurring, thereby sustaining the desired second stage of infusion shown in FIG. 4b where the coronary arteries are clearly segmented. The fine capillary bed of the myocardium 16 is perfused slowly by a very small number of microbubbles of the contrast agent. The velocity of bloodflow in a coronary artery supplying blood to a capillary bed will be relatively high, and as the volume of blood is distributed over the many capillaries of the bed the velocity becomes considerably lower in the capillaries. The bloodflow velocity increases again in the large collector vessels at the output of the capillary bed. Approximately five to eight cardiac cycles can be required to initially perfuse a capillary bed of the myocardium, or to reperfuse the capillaries after the contrast agent has been disrupted. By balancing the image frame rate (i.e., the transmit pulse rate) and the transmit pulse power, these very small microbubbles can be continuously disrupted as they begin to perfuse the myocardium. A higher frame rate and/or a higher transmit power will cause increased microbubble disruption in selected areas of. the cardiovascular system. It has been found that transmitting with a mechanical index setting of approximately 0.1 or less will cause little or no microbubble disruption, enabling the blood pool of the heart chamber, coronary arteries, and the myocardial capillary bed to be imaged at these levels. Above this level noticeable microbubble disruption will occur. In the range of a mechanical index of approximately 0.2–0.5, microbubbles are disrupted in substantial numbers before they are able to reperfuse the capillary bed in the image plane. Thus, imaging at these power levels will result in significant harmonic signal returns from the heart chamber and coronary arteries, which are significantly reinfused in the image plane between transmit pulses, with little signal returns from the capillary bed. At higher power levels, and particularly above a mechanical index of 1.0, there will be substantial microbubble disruption in the heart chamber, coronary arteries, and capillary bed, with only minor reinfusion of the image plane in the heart chamber blood pool. The exact numbers will vary for particular contrast agents. By use of a suitable low but disruptive mechanical index setting, the capillary bed of the myocardium can be effectively kept free of substantial amounts of contrast agent and hence will produce little if any harmonic contrast return signals. The result is that the second stage of FIG. 4b, where only the heart chamber and coronary arteries are producing significant harmonic return signals, can be maintained for a considerable period of time by proper selection of frame rate and transmit power. Combining selective disruption of the capillary bed with masking of the left ventricle blood pool enable the coronary arteries to be segmented for display. Another variation is to recognize the low velocity of flow in the myocardium as noted above, and to mask or reject signals of low flow velocity from the capillary bed.

Furthermore, the coronary artery imaging procedure can be controlled to reduce unwanted harmonic returns from contrast agent in the heart chamber, thereby minimizing the need for masking or other echo elimination techniques. The contrast agent can be administered through an intravascular catheter, which can be threaded into the aortic root. When the contrast agent is injected at the aortic root, the flow of blood out of the heart will prevent immediate entry of contrast agent into the heart chambers. Since the coronary arteries receive their blood supply from the aortic root, the injection of contrast agent at this location will cause the coronary arteries to immediately become infused with the agent. Thus the coronary arteries will be the first structure to light up with contrast agent, which will not enter the heart until traversing the vascular system and returning to the heart by venous flow, at which point a significant amount of agent may be eliminated by lung filtering. Thus, clutter from contrast agent in the heart chambers is reduced if not eliminated for at least the initial period of the procedure.

Figure 5A:
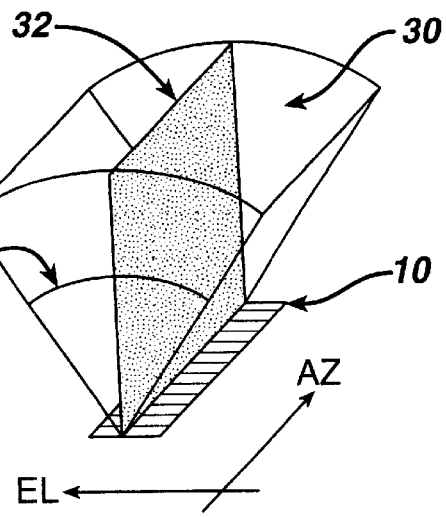
FIGS. 5a and 5b illustrate "slit-o-vision" scanning of a three dimensional volume with a linear and a phased array transducer.
Figure 5B:
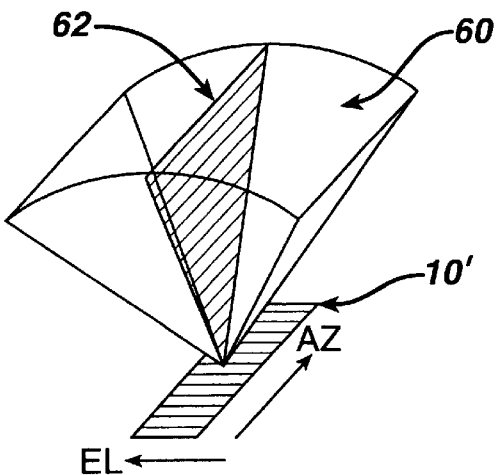

One way to form a planar ultrasonic projection image of a volumetric region is by means of the technique known as "slit-o-vision," which is described in U.S. Pat. No. 5,305, 756. In the slit-o-vision technique a volumetric region is insonified with an ultrasonic beam which is divergent in the elevation dimension and focused in the azimuth dimension. The technique takes its name from the fact that such an image can be formed by use of an aperture which is relatively long in the azimuth dimension and narrow in the elevation dimension. An ultrasound beam produced from such an aperture utilizes diffraction to radiate an essentially cylindrical wavefront that, while focused in azimuth, develops the desired divergence in the elevation direction. An elevationally divergent beam can also be produced by acoustic lenses or electronic lenses. For instance, when an element of an array is convex in the elevation dimension or has a lens which is elevationally divergent, elevationally divergent beams can be produced by a linear array 10 as shown in FIG. 5a. The elevation and azimuth dimensions are indicated by the EL and AZ arrows, respectively. The elevationally divergent beams will insonify a wedge-shaped volume 30. Points which are of the same range locus from the array 10, such as those along range locus 28, are acoustically integrated and projected at that range onto projection plane 32. This acoustic integration and projection occurs at every range in the volume, so that the entire volumetric region 30 is projected onto the projection plane 32. If the volumetric region contains only or principally signals from coronary arteries, the coronary arteries in the volume will be projected onto the projection plane 32 and appear as the image. FIG. 5b illustrates the same results from use of a phased array transducer 10', in which case the volumetric wedge 60 is more triangular and projects onto a triangular plane 62.

Figure 6A:
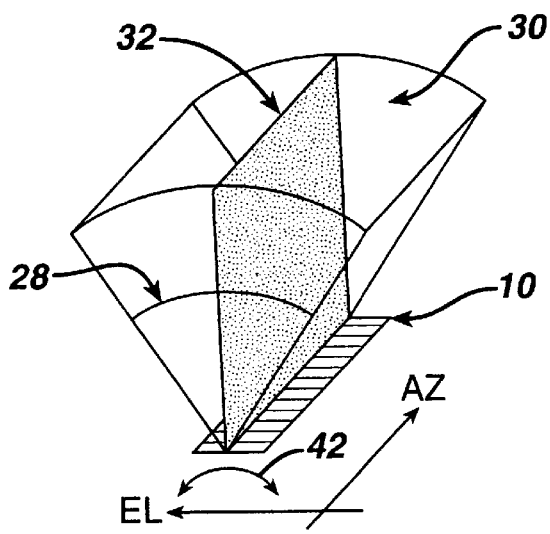
FIGS. 6a and 6b illustrate mechanical scanning of a three dimensional volume with a linear and a phased array transducer.
Figure 6B:
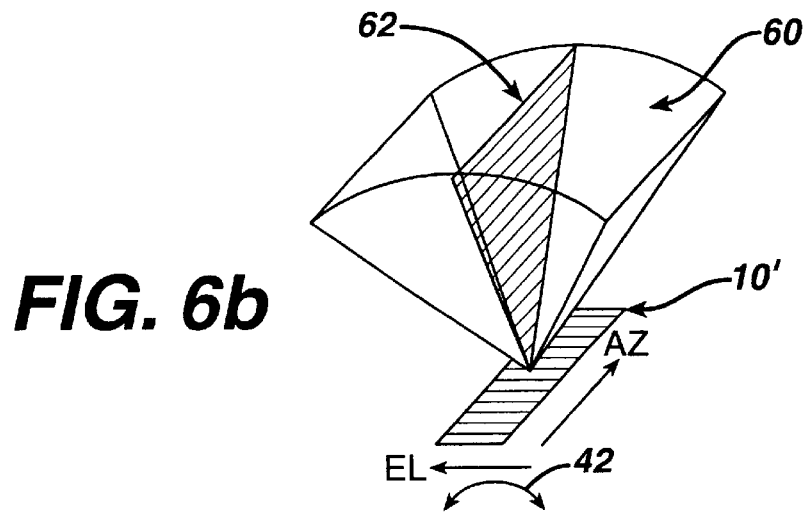

In FIGS. 6a and 6b the same volumetric regions 30 and 60 are insonified by sweeping beams focused in elevation and azimuth over the volumetric regions. This is done by rocking the 1D array in the elevation direction as shown by the arrows 42. After image planes within the volumes 30,60 have been acquired and contrast signals from the cavity have been removed, points of common range such as those along constant range locus 28 are integrated together to project the planes onto a common projection plane 32,62. Once again, an image in the form of an angiogram is formed when coronary artery information is predominate in the volumetric regions 30,60.

Figure 7A:
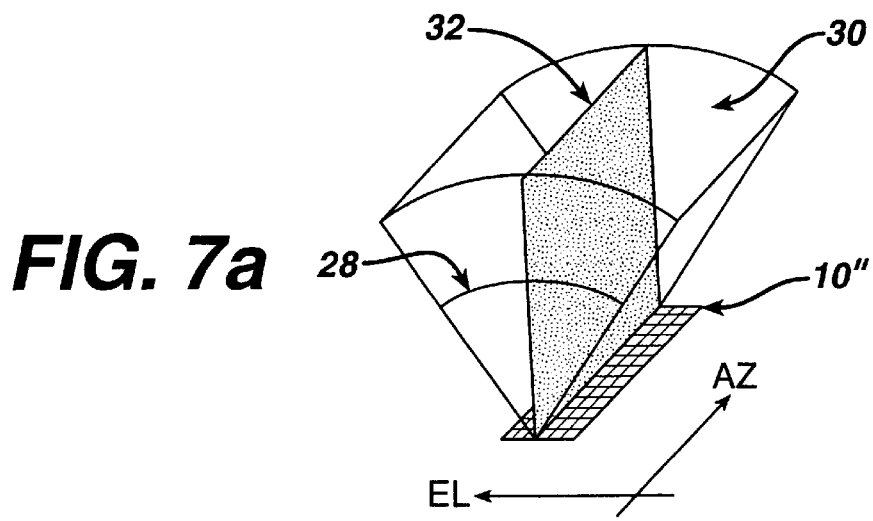
FIGS. 7a and 7b illustrate electronic slit-o-vision scanning of a three dimensional volume with two dimensional linear and phased array transducers.
Figure 7B:
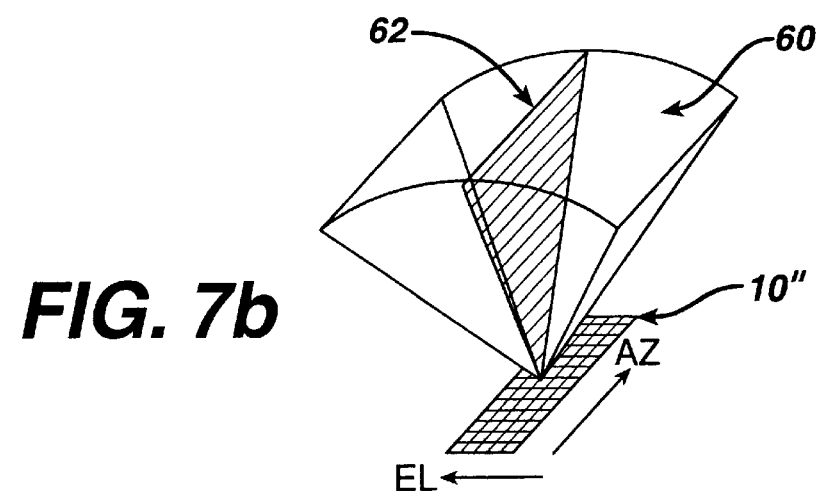

FIGS. 7a and 7b illustrate another slit-o-vision technique, in this case by the electronic synthesis of elevationally divergent beams, which has better sensitivity but generally lower frame rate than the embodiment of FIG. 5. These embodiments use two dimensional arrays 10", which may be operated as either 1.5D or 2D arrays. The transmit beams are made elevationally divergent by pulsing the central elevation elements first, then proceeding to pulse the outermost elevation elements last. FIG. 7a depicts a linear array scanning format which scans volumetric region 30, and FIG. 7b depicts a phased array scanning format which steers beams in a volumetric region 60. As in the case of the FIGS. 5a and 5b embodiments, points at a common range locus in the volumetric regions. acoustically integrate onto a projection plane 32 or 62 for a projection image of the structure in the volumetric regions 30 and 60. Alternatively, the 2D array of FIG. 7 can be focused and steered in elevation to effect the scanning of the volume as shown in FIG. 6.

Where discrete planes of a volumetric region are acquired as described below, they can be combined to form a projection image. as shown in FIG. 2 using volume rendering techniques. This three dimensional method has lower frame rates than the above "slit-o-vision" approaches, but provides greater spatial resolution, less clutter from off-axis reflectors, and more control over the image by variation of the rendering parameters.

Figure 8:
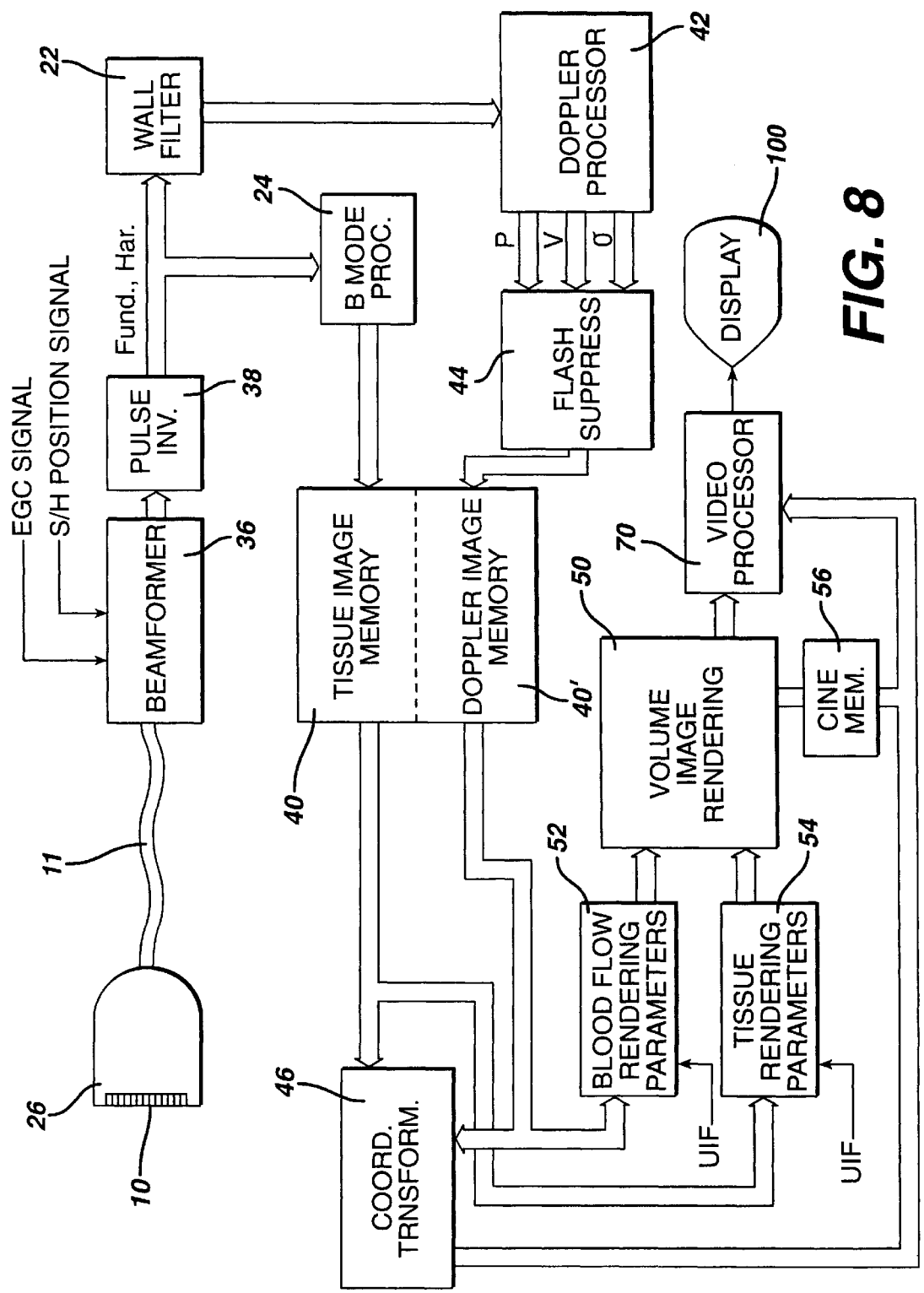
FIG. 8 illustrates an ultrasonic diagnostic imaging system constructed in accordance with the principles of the present invention.

FIG. 8 illustrates an ultrasonic diagnostic imaging system constructed in accordance with the principles of the present invention. A scanhead 26 including an array transducer 10 is connected by a cable 11 to a beamformer 36. The beamformer controls the timing of actuation signals applied to the elements of the transducer array for the transmission of steered and focused transmit beams, and appropriately delays and combines signals received from the transducer elements to form coherent echo signals along the scanlines delineated by the transmit beams. The timing of the beamformer transmission is also responsive to an ECG signal when it is desired to synchronize or gate image acquisition with a particular phase of the heart cycle. The beamformer is further responsive to a scanhead position signal when the transducer is being mechanically moved to sweep ultrasonic beams over a volumetric region, thereby enabling beams to be transmitted when the transducer is properly oriented with respect to the volumetric region.

The output of the beamformer is coupled to a pulse inversion processor 38 for the separation of fundamental and harmonic frequency signals. Pulse inversion processors are well known in the art and are described in U.S. Pat. Nos. 5,706,819 and 5,951,478. These patents describe how echoes from alternately phased pulses can be used to separate harmonic contrast signals from fundamental signals, which is a preferred method of separating signals from contrast agents for coronary imaging in accordance with the present invention.

The fundamental and/or harmonic signals maybe be B mode processed or Doppler processed, depending upon the desired information to be displayed. For Doppler processing the signals are coupled to a wall filter 22 which can distinguish between flow, stationary tissue, and moving tissue. A preferred wall filter for contrast imaging is described in U.S. Pat. No. 6,095,980, which is also capable of performing harmonic contrast signal separation. The filtered signals are applied to a Doppler processor 42, which produces Doppler power, velocity, or variance estimation. A preferred Doppler processor for harmonic Doppler signal estimation is described in U.S. Pat. No. 6,036,643. Artifacts from scanhead motion which can contaminate Doppler imaging are removed by a flash suppressor 44. Various techniques may be used to remove flash artifacts prior to or subsequent to image formation, including the notch filter technique described in U.S. Pat. No. 5,197,477 and the min-max filter technique described in U.S. Pat. No. 5,782,769. The processed Doppler signals are stored in a Doppler image memory 40'.

Signals which are to be B mode processed are applied to a B mode processor 24 which detects the signal amplitude. B mode processed signals are stored in a tissue image memory 40.

The B mode and Doppler signals are applied to a coordinate transformation processor 46. For conventional two dimensional imaging the coordinate transformation processor will function as a scan converter, converting polar coordinates to Cartesian coordinates as necessary and filling spaces between received lines with interpolated image data. The scan converted images are coupled to a video processor 70 which puts the image information into a video format for display of the images. on a display 100. The images are also coupled to a Cineloop® memory 56 for storage in a loop if that function is invoked by the user.

When 3D imaging is being performed by the ultrasound system, the coordinate transformation processor may be used to scan convert the tissue and Doppler signals in planes of image information over the scanned volume, or may be used to transform the coordinates of the image data into a three dimensional data matrix. Preferably the coordinate transformation processor operates in cooperation with a volume rendering processor 50, which can render a three dimensional presentation of the image data which has be processed by the coordinate transformation processor. Three dimensional images of tissue are rendered in accordance with tissue rendering parameters 54 which are selected by the user through a control panel or user interface (UIF). Three dimensional images of Doppler information are rendered in accordance with blood flow rendering parameters 52. These parameters control aspects of the rendering process such as the degree of transparency of tissue in the three dimensional image, so that the viewer can see the vasculature inside the tissue. This capability is important when 3D images of both tissue and flow are being rendered, as described in U.S. Pat. No. 5,720,291. Three dimensional images can be stored in the Cineloop® memory 56 and replayed to display the scanned volume in a dynamic parallax presentation, for instance. A three dimensional rendering of flow without the surrounding tissue, as described in U.S. Pat. No. Re 36,564, can reveal the continuity of flow of blood vessels and obstructions in those vessels and is useful for coronary artery diagnosis in accordance with the present invention.

Different transducer-probes can be used to scan a volumetric region of the heart which includes the coronary arteries. Either a 1D (azimuth steered) or a 1.5D or 1.75D (azimuth steered and elevation focused) array may be moved mechanically to sweep beams over the three dimensional volume. For electronic steering either a 1.75D ( minimally electronically steered in azimuth and elevation) or a 2D (fully electronically steered in azimuth and elevation) array may be used. An embodiment which uses a 2D array transducer 10" is shown in FIG. 9. An important consideration in the use of two dimensional arrays is the number of cable wires used to connect the probe to the ultrasound system. Various approaches can be used to reduce the number of cable conductors and thus the size of the cable, including wireless links to the ultrasound system, microbeamforming in the probe, digital or analog time multiplexing, the use of sparse arrays, and the use of transmit/receive multiplexers. One solution is an r.f. probe which transmits echo signals wirelessly to the ultrasound system as described in U.S. Pat. No. 6,142,946. Another solution, when a cable connection is used, is to partition the beamformer between the scanhead and the ultrasound system as described in U.S. Pat. No. 6,102,863. The embodiment of FIG. 9 makes use of this approach by performing elevation beamforming in the scanhead 26 and azimuth beamforming in the ultrasound system 101. For example, suppose that the two dimensional array has 128 columns of elements extending in the azimuth direction (indicated by the AZ arrow in the drawing) and six rows of elements in the elevation direction (indicated by the EL arrow). If each element of the array were connected by its own conductor to the ultrasound system, a cable of 768 signal conductors would be required. In the embodiment of FIG. 9 each column of six elements is coupled to an elevation beamformer 36a which appropriately excites (on transmit) and delays and combines (on receive) signals from the six elements of the column. This combines the six signals in each column into one elevation beamformed signal, which is then coupled over a cable conductor to the ultrasound system, where the elevation beamformed signals are beamformed in the azimuth direction. In the foregoing example, the 128 elevation beamformed signals are coupled over the 128 conductors of a cable 11, a significant reduction in cable size as compared to a probe without scanhead beamforming. At least elevation steering is performed in the elevation beamformer 36a, and preferably both steering and focusing are performed in the elevation beamformer.

The operation of the elevation beamformer is illustrated in FIGS. 10a and 10b. In FIG. 10a a beam is being steered normal to the array transducer as indicated by the 0° arrow extending from the elements $10_1$ through $10_n$, which comprise a column of elements in the elevation direction. Signals at the center of the column are delayed more than signals at the ends of the column as indicated by the relative length of the delays 102 for the different elements to effect a focus. Delayed receive signals are combined by a summer 104, then coupled over a signal lead in the cable 11 to the azimuth beamformer 36b. FIG. 10b illustrates the situation when a beam is to be transmitted or received from the left at a 30° inclination in elevation as indicated by the 30° arrow. In this case signals on the left side of the array are more greatly delayed as indicated by the relative length of the delays 102. Received signals are combined by the summer 104 and coupled through the cable to the azimuth beamformer 36b.

FIGS. 11a–11c illustrate the implementation of the elevation beamformer in three different ways (neglecting any buffering or gain elements). FIG. 11a illustrates an analog implementation in which each transducer element $10_m$ is coupled to an analog delay line 106. The length of the delay is set by choosing the input or output tap of the delay line and the delayed signals are coupled to an analog summer or to an A/D converter if the signals are to be digitally combined. In FIG. 11b each transducer element $10_m$ is coupled to a CCD delay line 108. The length of the delay is set by choosing an input or output tap that determines the number of charge storage elements in the delay line or by varying the rate at which the charge samples are passed through the charge storage elements. The outputs of the delay lines are summed either in sampled analog format or after being digitized.

FIG. 11c illustrates a digital embodiment of an elevation beamformer. In this example the elevation beamformer has 128 sub-beamformers 120, each processing the signals from one elevation column of six transducer elements. Each of the transducer elements $10_1$ through $10_n$ is coupled to an A/D converter 110 and the digitized signals are delayed by a digital delay line 112, which may be formed by a shift register, FIFO register, or random access memory. The appropriately delayed signals are combined in a summer 104 and coupled over cable conductors to the azimuth beamformer. To conserve cable conductors when using multibit signal samples, the data values from several of the beamformer channels 120 can be interleaved (time multiplexed) and sent over the same group of conductors at a data rate sufficient for the desired level of realtime imaging performance.

FIG. 12 illustrates the organization and control of a number of beamformer channels 120 of a scanhead elevation beamformer. The beamformer comprises N elevation sub-beamformers $120_1$–$120_n$ where each sub-beamformer receives signals from a column of transducer elements in the elevation direction, as indicated by the number 6 for this example. Data to control the elevation beamforming (such as elevation angle and focusing) is sent to a timing & delay decoder & data store 126 in the scanhead 26, preferably serially over a cable conductor. This control data is decoded and delay values coupled to a delay control 124, which sets the beamformer channels for the desired delays for each transducer element. For dynamic focusing the delays are changed as echoes are received. The elevation aperture can be varied by applying zero weights to some of the outermost channels when a smaller (near field). aperture is desired. The data received by the timing & delay decoder & data store 126 is also used to control transmit timing by pulse transmitters $122_1$–$122_n$, each of which controls the transmission of the six transducer elements in an elevation column in this example. When received echo signals are processed in the analog domain as illustrated by FIGS. 11a and 11b, the signals from the 128 channels of the elevation beamformer in this example are sent over 128 cable conductors to the azimuth beamformer 36b. When the echo signals are processed digitally the signals from the 128 channels are interleaved (time multiplexed) and sent over digital conductors of the cable 11 to the azimuth beamformer in the ultrasound system 101.

Figure 13:
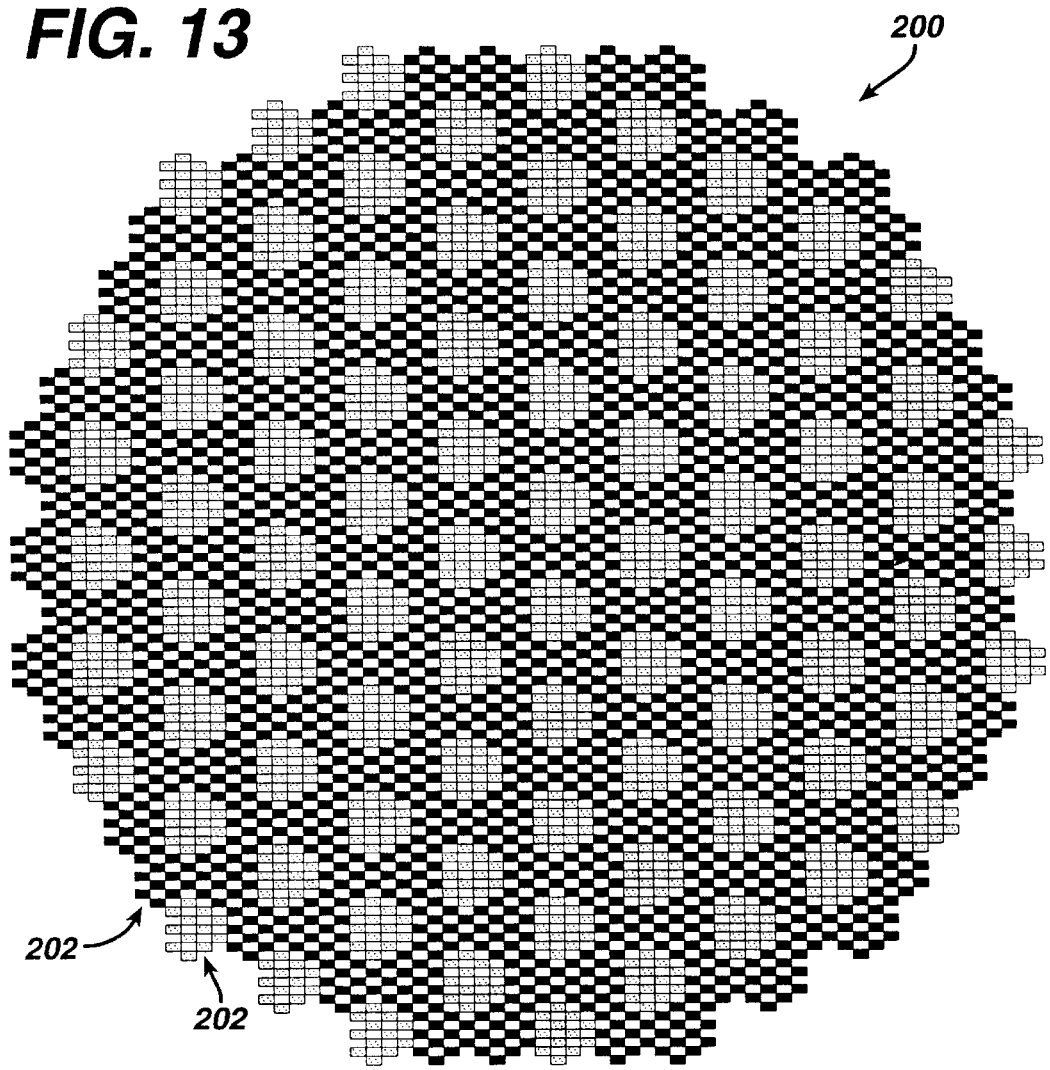
FIG. 13 is a plan view of a two dimensional transducer array for three dimensional scanning in accordance with the present invention.

A true 2D electronically steered embodiment of the present invention is illustrated starting with FIG. 13. This drawing shows a plan view of a 2D transducer array 200 of greater than three thousand transducer elements. For ease of illustration the small boxes in the drawing which represent individual transducer elements are shown spaced apart from each other. However, in a constructed embodiment, the individual transducer elements are close packed in a repeating hexagonal pattern. The 2D array has an overall dodecahedral outline. In a preferred mode of operation beams are transmitted outward from the center of the array and can be steered and focused in a cone of at least ±30° about a line normal to the center of the array.

When steered straight ahead, echoes received from along a transmitted scanline are initially received at the center of the array and then in circular or arcuate groupings of elements centered on and extending outward along the projection of the scanline onto the surface of the array. In the illustrated embodiment approximately the central one-quarter of the elements are used for beam transmission. The entire array is available for echo reception.

Figure 14:
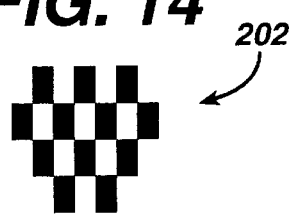
FIG. 14 illustrates a receive sub-aperture of the transducer array of FIG. 13.

The array 200 of FIG. 13 is seen to be drawn in alternate light and dark groupings 202 of twelve transducer elements. One of these groupings 202, referred to herein as a "patch" of transducer elements, is shown in a separate enlarged view in FIG. 14. These irregular hexagonal patches 202 of twelve elements are beamformed together during echo reception as discussed in detail below. Elements in the center of the array (approximately 750 elements) are connected in groups of three for transmission by high voltage mux switches. FIGS.

Figure 15:
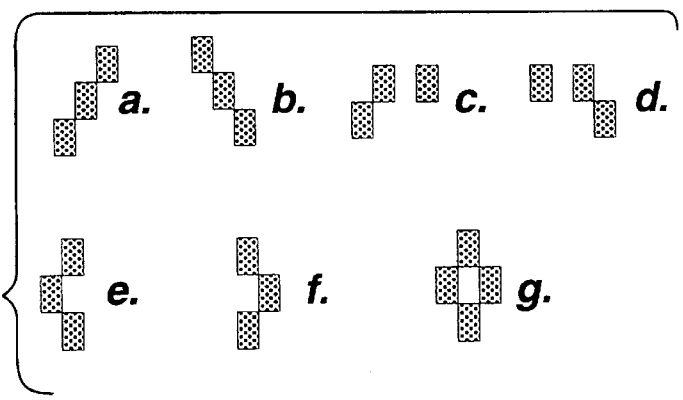
FIGS. 15a–15g illustrate different transmit sub-apertures of the transducer array of FIG. 13.

15a–15f show some of the three-element configurations that are possible during beam transmission. The transmit groupings can also simply be three elements adjacent to each other in a straight line. The exact configuration or configurations used to transmit a given beam depend upon the desired beam characteristics and its azimuth. Four elements may also be connected together for transmission as illustrated by the diamond shaped grouping of four elements in FIG. 15g.

Since a cable with more than three thousand conductors is not currently practical, each patch of twelve elements of the array is beamformed in the scanhead. This reduces the number of signals which must be coupled to the ultrasound system beamformer to approximately 256. Then, a 256 channel beamformer in the ultrasound system can be used to beamform the partially beamformed signals from the scanhead.

Because the elements of each receive patch of twelve elements of the 2D array are sufficiently small, contiguously located, and closely packed, the echo signals received by the elements of a patch will be aligned to within one wavelength at the nominal receive frequency for steering angles of approximately 40° or less (neglecting focal delays). The echoes of the elements are then sampled to bring all of the patch element signals into precise time alignment. The sampling is done with a range of sampling delays with a precision of a fraction of a wavelength to bring the signals from all of the patch elements to a time alignment within the precision of the sampling clock quanta, preferably $\frac{1}{16}$ of a wavelength or less. The time-aligned signals from the patch elements are then combined. This beamforming of each patch is done by microelectronics located immediately behind the transducer array in the scanhead to facilitate interconnections. Sample time shifting and alignment is performed by the sampling delay line shown in FIGS. 16 and 17. Each element 204 of a patch of elements which is to be partially beamformed is coupled by way of an amplifier 206 to a sampling input switch 208. The sampling input switch 208 is continually conducting samples of the transducer signal onto capacitors 212 in a sequential manner. The sequencing of the switch 208 is under control of a ring counter 210 which is incremented by a clock signal. As the darkened segment of the ring illustrates, the sampling input switch is continually sampling the input signal onto successive ones of the capacitors 212 in a circular manner. The amplifier 206 has a bipolar output drive so that the charge of a capacitor can be either increased or decreased (discharged) to the instantaneous signal level at the time of sampling.

The signal samples stored on the capacitors 212 are sampled by a sampling output switch 214 which samples the stored signals in a sequential manner under control of a second ring counter 216. As shown by the darkened segment on the ring of the second ring counter 216, the sampling output switch 214 samples the stored signals in a particular time relationship to the input switch and its ring counter. The time delay between the input and output sampling is set by a time shifter 220 which establishes the time delay between the two ring counters. Thus the time of sampling of the output signal samples can be incrementally advanced or delayed as a function of the timing difference between the two ring counters. This operation can be used to bring the output signal samples of all the elements of a patch into a desired time alignment such as the sampling time of a central element of the patch. When the signals from all of the elements of the patch are within a desired range of sampling time, the signals can be combined into one signal for further beamforming in the ultrasound system. The time aligned output signals are further amplified by an amplifier 218 and coupled to a summer for combining with the signals of the other elements of the patch.

Figure 16:
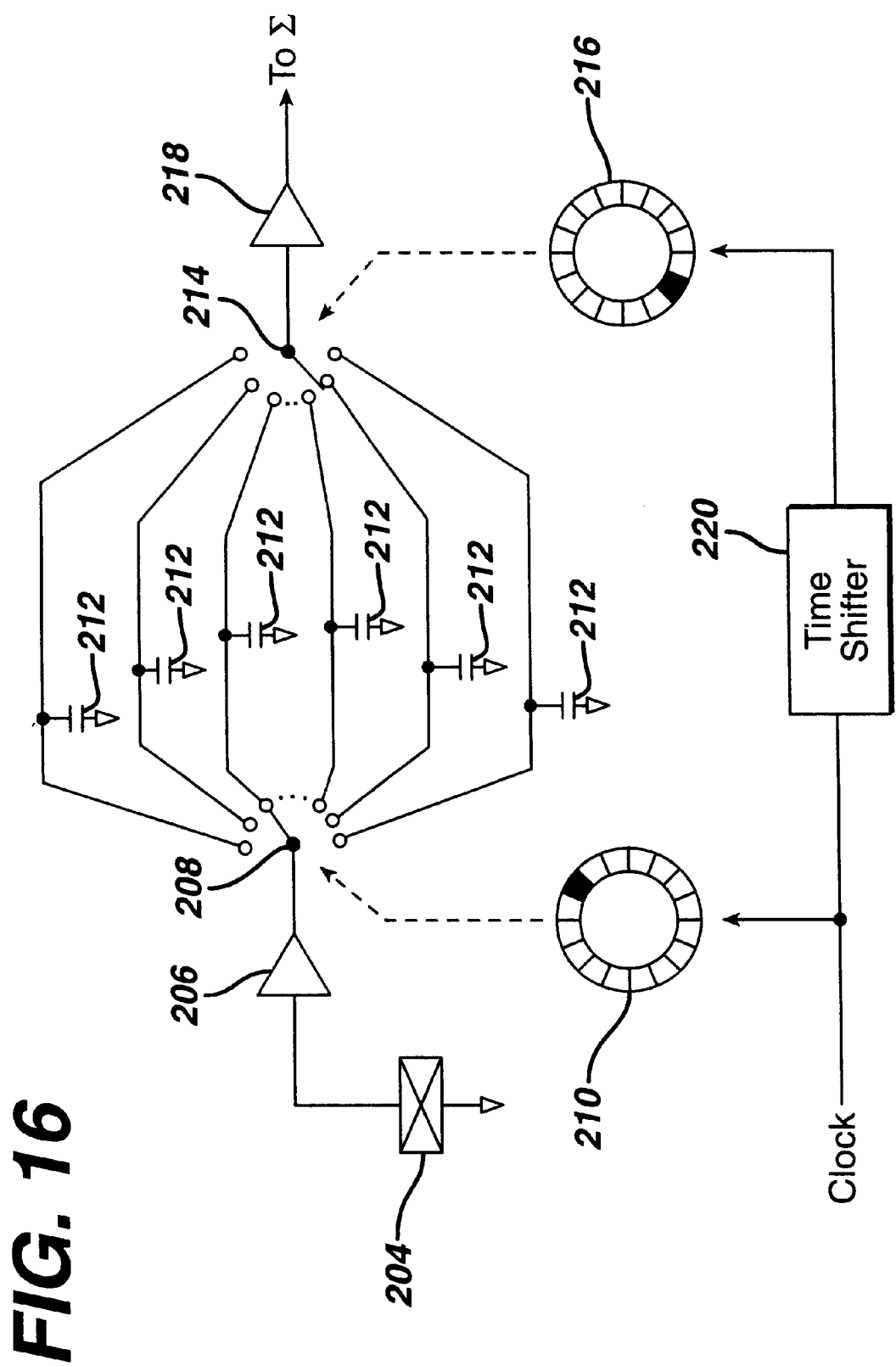
FIG. 16 illustrates scanhead microcircuitry for sampling the signals received by a transducer element of the transducer array of FIG. 13 in a desired time relationship.
Figure 17:
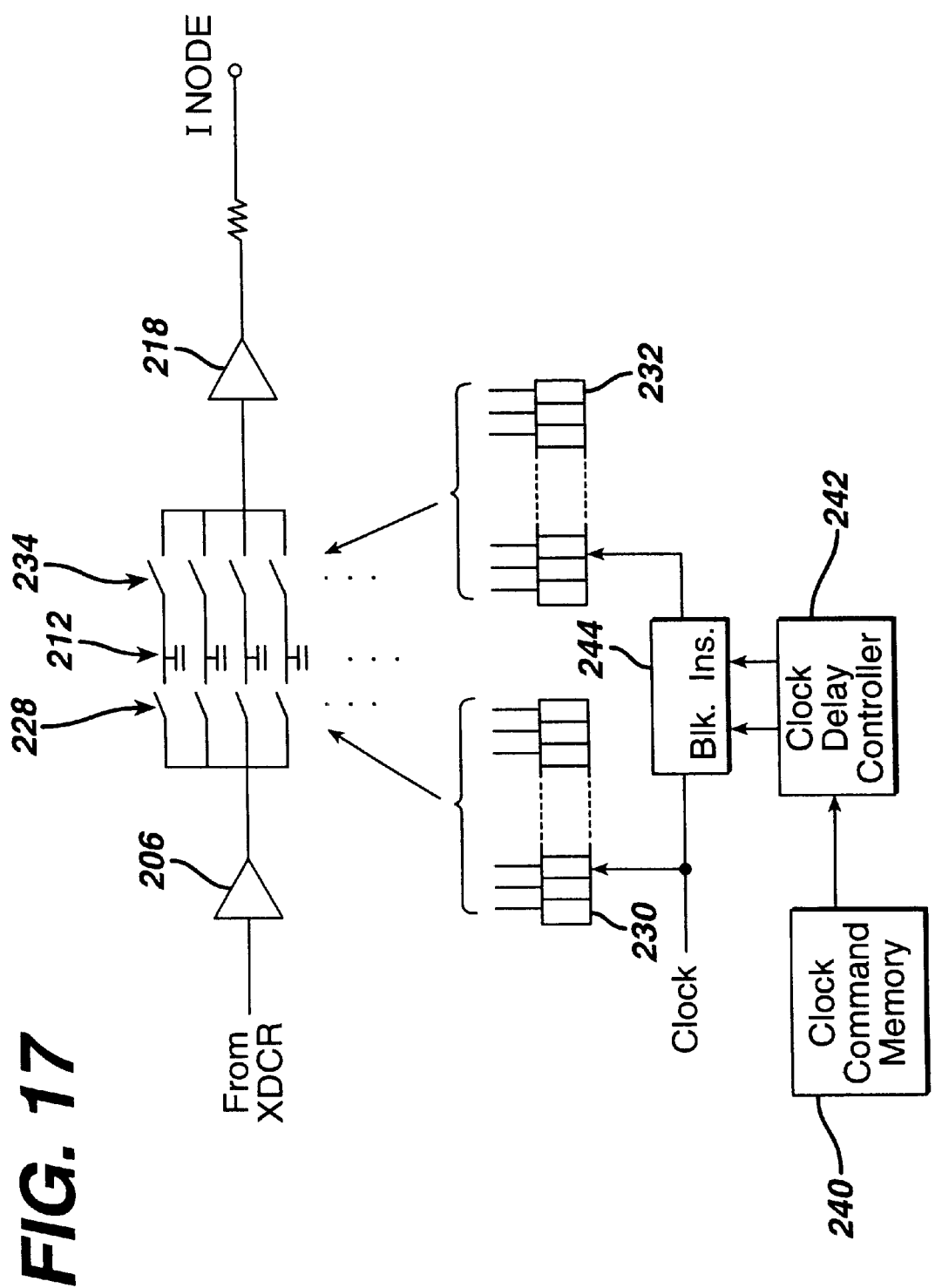
FIG. 17 is a more detailed view of the microcircuitry of FIG. 16.

Details of a constructed embodiment of the arrangement of FIG. 16 are shown in FIG. 17. In integrated circuit fabrication the sampling switches do not have rotating wipers as illustratively shown in FIG. 16, but are formed by a plurality of gates 228. Each of the gates 228 is controlled by the output of an output stage of a shift register 230, which is arranged to circulate one bit and thereby operate as a ring counter. When the bit is shifted to a particular stage of the shift register 230, the gate 228 connected to that stage is closed to conduct a signal sample to its capacitor 212. The output switches are similarly constructed as a series of parallel gates 234, and are similarly controlled by stages of circulating shift register 232. Signal samples taken from the capacitors 212 are amplified and resistively coupled to a current summing node for summation with the other signals of the grouping.

A clock command memory 240 is located in the scanhead and preferably on the same integrated circuit as the sampling circuitry. The clock command memory stores data identifying the time delays needed for one or more receive echo sequences. The control data for the current beam is coupled to a clock delay controller 242 which controls the relative time relationship between the two ring counters. The controller 242 does this by blocking clock cycles applied to the first ring counter 230 from reaching the second ring counter 232, or by inserting additional clock cycles into the clock signal. By blocking or inserting shift register clock pulses to the second ring counter the relative timing between the two ring counters is adjustably advanced or retarded. The time aligned samples from all of the transducer elements of the patch are then combined at a current summing node I Node. The summed signals from the patch are coupled through the scanhead cable to the ultrasound system beamformer.

With the addition of a second sampling output switch for each element controlled in a different time relationship than the first sampling output switch, and a second summer for the second sampling output switches of the patch elements, a second, receive beam can be produced at the same time as the first receive beam. Thus, each patch becomes a small multiline receiver receiving two (or more) receive beams simultaneously, which is useful in the multiline embodiment described below.

The microbeamformer for the patches can utilize other architectures such as charge coupled delay lines, mixers, and/or tapped analog delay lines.

Figure 18A:
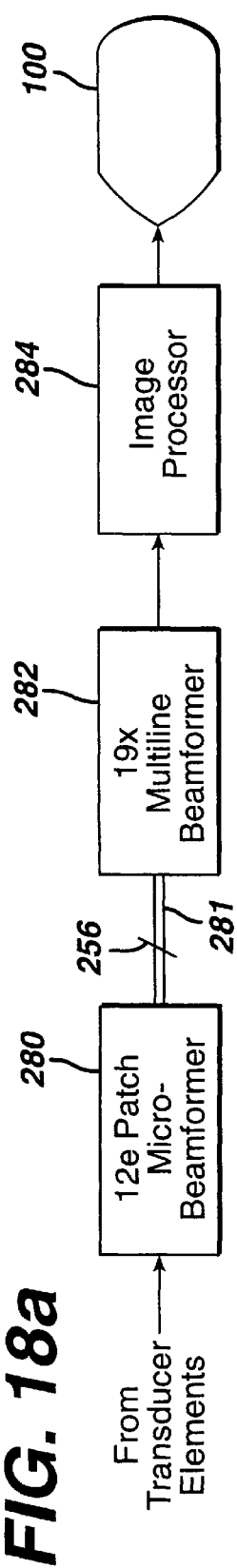
FIG. 18a illustrates a scanhead micro-beamformer and multiline beamformer system suitable for processing the signals received by the transducer array of FIG. 13.
Figure 18B:
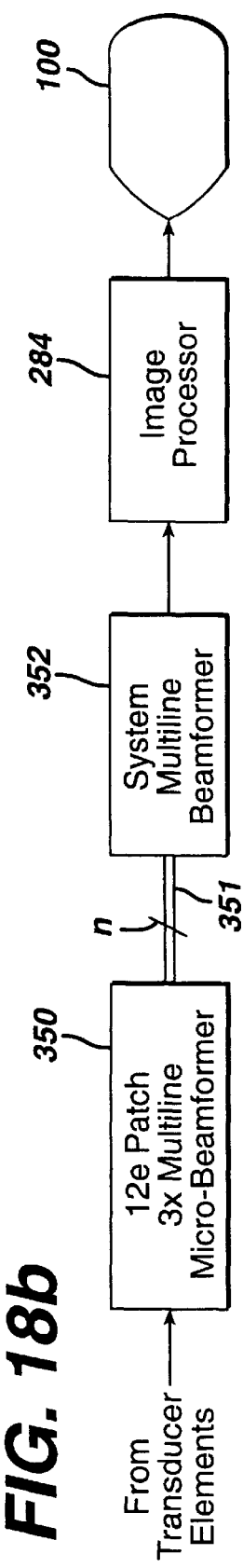
FIG. 18b illustrates the use of a multiline scanhead micro-beamformer in combination with a system multiline beamformer.

Three dimensional imaging requires that the volumetric region be sufficiently sampled with ultrasound beams over the entire volume. This requires a great many transmit-receive cycles which causes the time needed to acquire a full set of volumetric data to be substantial. The consequences of this substantial acquisition time are that the frame rate of a realtime 3D display will be low and that the images will be subject to motion artifacts. Hence it is desirable to minimize the time required to acquire the necessary scanlines of the volumetric region. A preferred approach to this dilemma is to employ multiline beamforming, scanline interpolation, or both, as shown in FIGS. 18 and 19. While beams may be steered in a square or rectangular pattern (when viewed in cross-section) to sample the volume being imaged, in a preferred embodiment the beams are oriented in triangular or hexagonal patterns in the volumetric region to sufficiently and uniformly spatially sample the region being imaged. FIG. 19a is a cross-sectional view through the volumetric region in which scanlines in the volumetric region are axially viewed. In this example nineteen scanlines are produced for every transmit beam. The scanline locations are spatially arranged in hexagonal patterns. The nineteen scanline locations of one hexagonal pattern are denoted by circles which represent axial views along the scanlines. The nineteen scanline locations are insonified by a "fat" transmit beam of a desired minimum intensity across the beam. The transmit beam in this example is centered on the location of scanline 270, and maintains the desired acoustic intensity out to a periphery denoted by the dashed circle 250, which is seen to encompass all nineteen scanline locations. The echoes received by the elements of the transducer array are partially beamformed by a micro-beamformer 280 in the scanhead as described above and coupled to a 19×multiline beamformer 282 in the ultrasound system as shown in FIG. 18a. In this example a 2D transducer array of 3072 elements is operated in patches of 12 elements, producing 256 patch signals which are coupled to the ultrasound system by a cable 281 with 256 signal conductors without multiplexing. The 19×multiline beamformer processes the 256 echo signals received from the transducer patches with nineteen sets of delays and summers to simultaneously form the nineteen receive scanlines 252–274 shown in FIG. 19a. The nineteen scanlines are coupled to an image processor 284, which performs some or all of the harmonic separation, B mode, Doppler, and volume rendering functions previously described in FIG. 8. The three dimensional image is then displayed on the display 100.

Figure 19A:
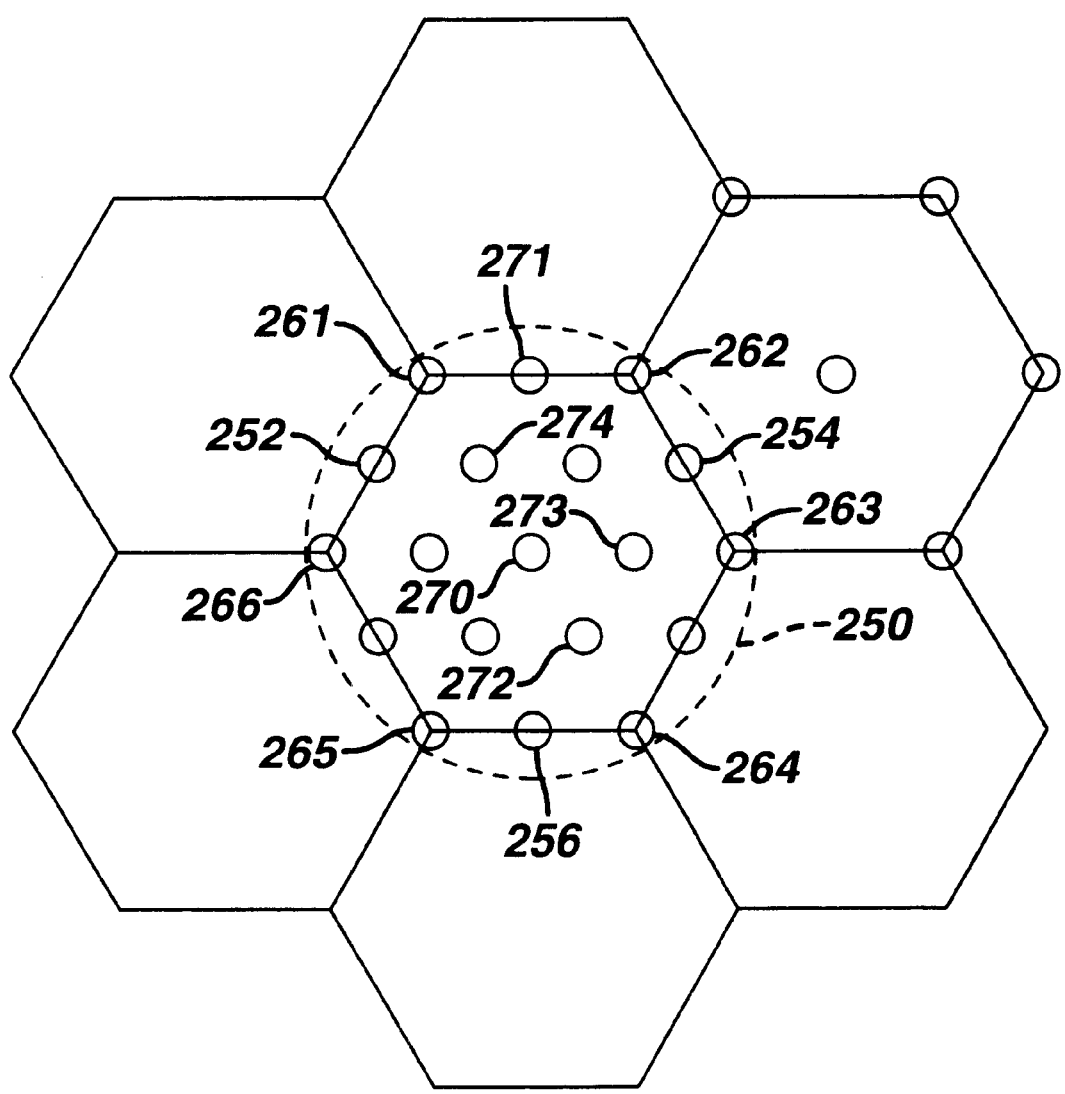
FIG. 19a illustrates operation of the system of FIG. 18a for a hexagonal scanning pattern.
Figure 19B:
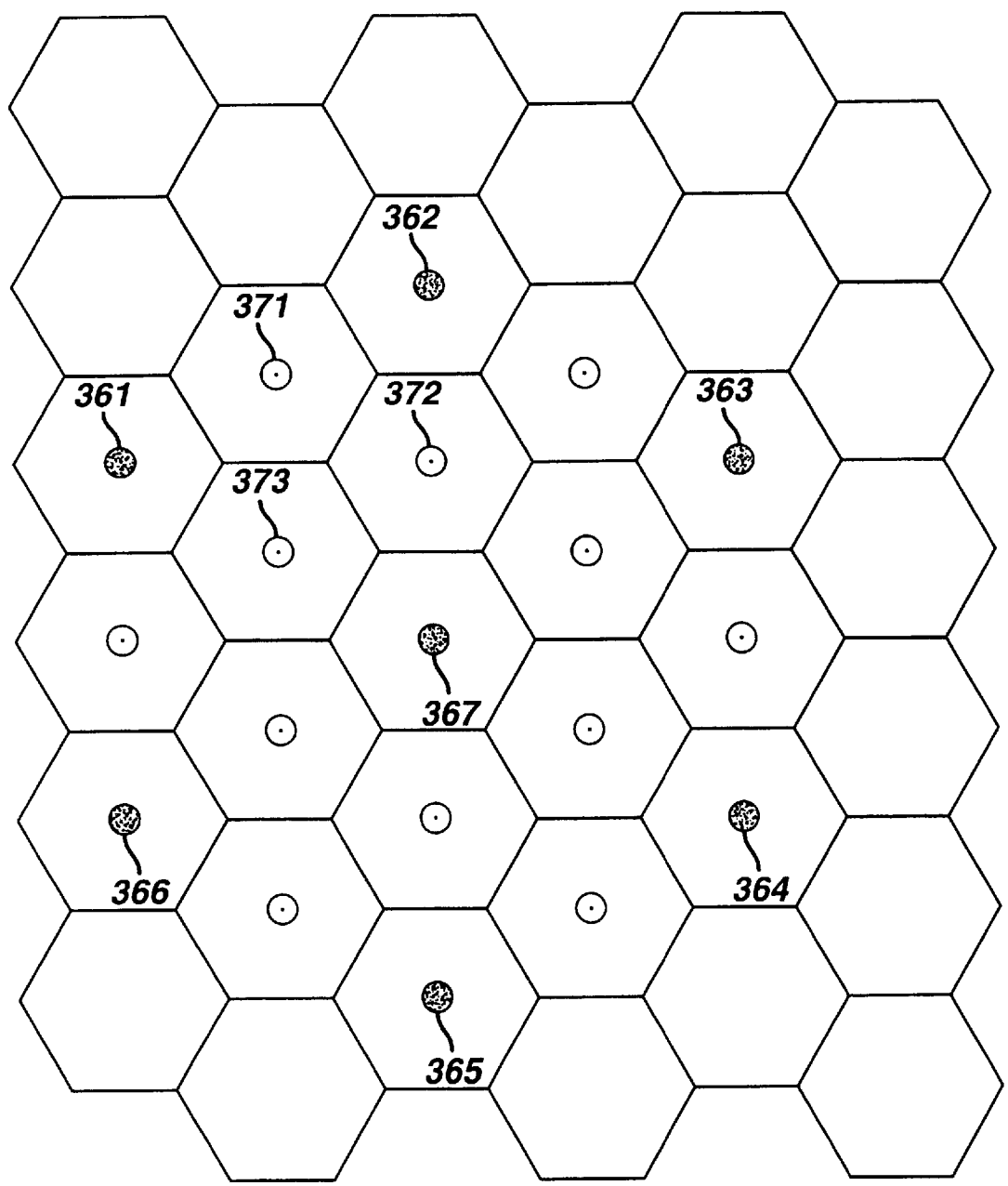
FIGS. 19b and 19c illustrate the use of interpolation to develop a hexagonal scanline pattern.

Interpolation may be used to form scanline data, either alternatively to or in conjunction with multiline scanline formation. FIG. 19b illustrates a series of scanlines 361–367 marked by the darkened circles which have been acquired from a volume being imaged in a hexagonal pattern as indicated by the background grid pattern. The scanlines 361–367 can be acquired individually or in groups of two or more by multiline acquisition. Scanlines at the undarkened circle locations are interpolated from the acquired scanlines using two-point r.f. interpolation. The interpolated scanline 371 is interpolated by weighting each of the adjacent scanlines 361 and 362 by ½, then combining the results. The weights used are a function of the location of the scanline being produced in relation to the locations of the three received scanlines whose values are being interpolated. Similarly, interpolated scanline 372 is interpolated using adjacent scanlines 362 and 367, and interpolated scanline 373 is interpolated using adjacent scanlines 361 and 367. Each group of three scanlines is used to interpolate three intermediate scanlines using weighting factor which are a factor of two ($2^{-1}$), enabling the interpolation to be performed rapidly by shifting and adding the bits of the data being interpolated. This avoids the use of multipliers and multiplication and affords high-speed processing advantageous for realtime 3D display rates.

Figure 19C:
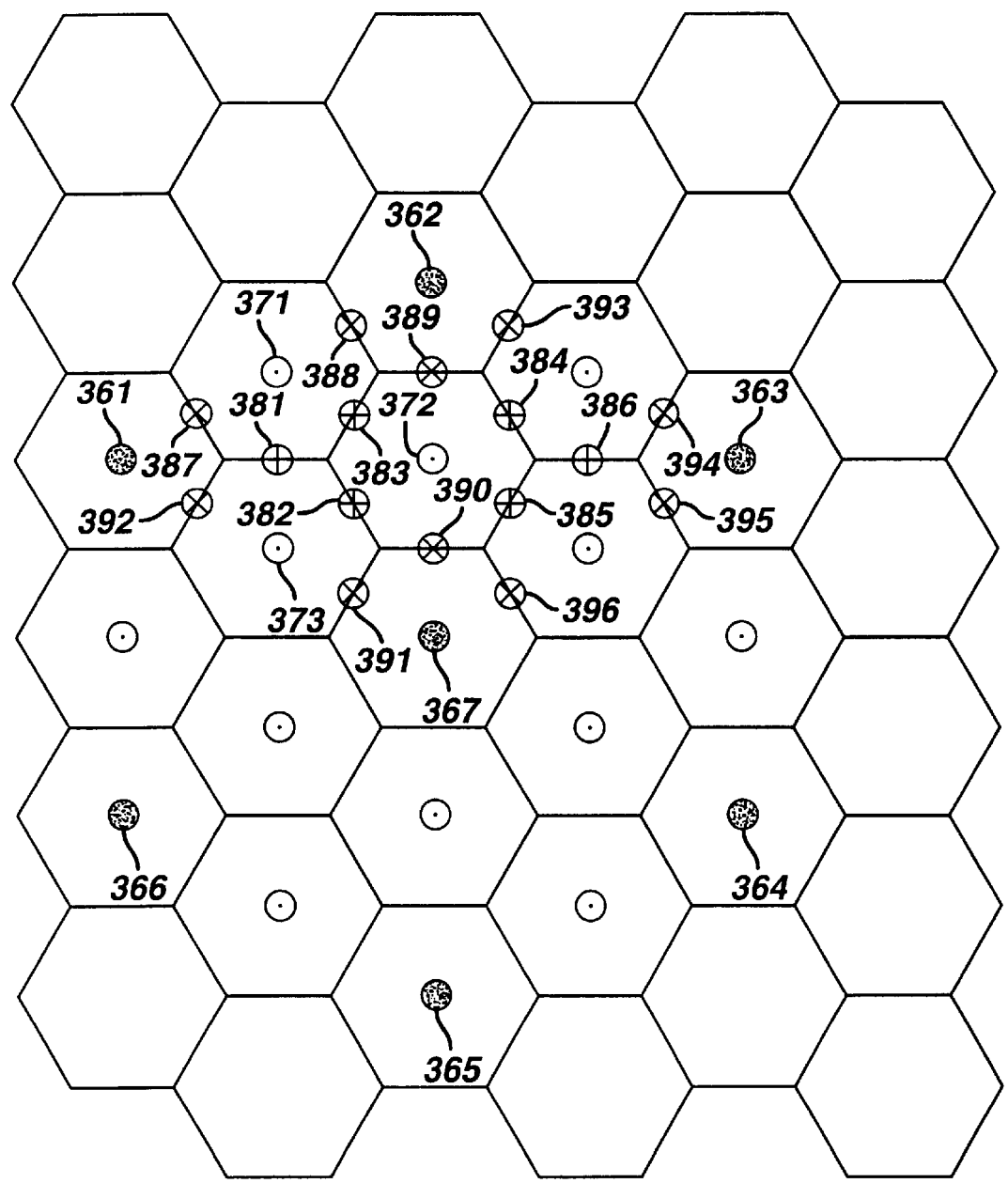

FIG. 19c illustrates a further iteration of the interpolation of FIG. 19b in which the scanline density of the volume is increased even further by interpolation. In this illustration two further sets of scanlines 381–383 and 387–392 are interpolated between the previous set. These scanlines may be interpolated using the previously interpolated set of scanlines, or they may be interpolated directly (and simultaneously, if desired) from the acquired scanlines 361, 362,367. These scanlines also have the advantage of being weighted by weighting factors which are a factor of two. The set of interpolated scanlines most central to the three received scanlines, 381–383, are interpolated using weighting factors of ½ and ¼. Scanline 381, for instance, is produced by (½ (scanline 361)+ ¼(scanline 362)+¼ (scanline 367)). The outer set of scanlines is produced by ¼, ¾ weights as described in U.S. Pat. No. 5,940,123. Scanline 392, for instance, is produced by (¼(scanline 367)+¼ (scanline 361)) or, to avoid multiplication, (¼(scanline 367)+¼(scanline 361)+¼(scanline 361)+¼(scanline 361)). FIG. 19c illustrates corresponding sets of interpolated scanlines for received scanlines 362,363,367, including the central group of scanlines 384–386, and the outer set of scanlines 393–396. To reduce motional artifacts, the received scanline data can be filtered in either r.f. or detected form prior to display.

The above example uses a linear interpolation filter kernel. It is also possible to use an interpolation kernel that has a non-liner shape (such as, for example, cosine, sinc, etc.) However the filter coefficients of these other filters will generally not have the desirable power of two property.

The use of patches to reduce the size of the cable needed to connect the scanhead to the ultrasound system may, under certain operating conditions, give rise to undesired grating lobes in the scanhead's beam pattern. This is due to the grouping of individual transducer elements into a single unit, giving the transducer array a coarser pitch, even with the use of micro-beamforming as described above. This problem can be reduced by considering each patch to be a sub-aperture of the entire 2D array which is capable of receiving signals from multiple, closely spaced scanlines in the transmit beam field. The signals from the sub-apertures can be delayed and summed to form a group of multiline received scanlines. Grating lobes which arise by reason of the periodicity of the sub-apertures and can contribute clutter to the final image are reduced by producing two or more differently steered signals from each sub-aperture (patch). The steering difference is kept small, within the beamwidth of the patch. By keeping the steering delay profile less than $\lambda/2$, significant grating lobes are kept out of the image field.

A simple 1D example illustrates these effects. Consider a sixty-four element 1D linear array with inter-element spacing (pitch) of $\lambda/2$. The array is divided into four patches of sixteen elements each. Two beams are steered to the left and right of a nominal direction on each patch. The steering angles are limited so that other lines or samples can be interpolated between these two received multilines. It is desirable for the multilines to be radially far enough apart to support the creation of interspaced interpolated lines, but close enough together so that r.f. interpolation will not form artifacts due to spatial undersampling. For example, if the steering delays are limited to correspond to less than $\pm\lambda/8$, then the two steered beams from each patch will fall within approximately the −1 dB width of the nominal patch beampattern. Also, because the steering delay between the left and right multiline on any element is thus limited to $\lambda/4$, r.f. interpolated lines can be produced using a simple two tap interpolation filter ($\lambda/2$ delays would correspond to the Nyquist criterion). The $\lambda/8$ delay limitation limits the steering angle to approximately $\pm(\lambda/8)/(4*\lambda)$ or $\frac{1}{32}$ radians. Thus the angle between the left and right multilines can be about $\frac{1}{16}$ radians, or about 3.6 degrees. If two other lines are symmetrically interpolated between the two received multilines, the resulting line spacing is approximately 1.2 degrees. A greater number of more closely spaced multilines or interpolated lines can also be produced as desired.

In the 1D array example, instead of producing a single scanline from each patch steered in the nominal steering direction, two scanlines are produced, one steered slightly left of the nominal steering direction and one steered slightly right. In the case of a 2D array, several variations are possible. For a rectilinear 2D array, four scanlines are produced for each patch, steered left, right, up and down in quadrature relationship. For a triangular-based 2D array such as a hexagonal array, three scanlines are produced at rotations of 120° as shown in FIG. 18d. The scanlines produced in this drawing are identified as $B_{\phi 0}$, $B_{\phi 120}$ and $B_{\phi 240}$, respectively, where the subscript number refers to the direction of rotation in the plane normal to the nominal steering direction of the patch and the angle $\phi$ is the. small angle at which each scanline is tilted from the nominal steering direction. The angle $\phi$ is kept small as described above so that the three scanlines are kept within the beamwidth of the nominally steered beam.

Figure 18C:
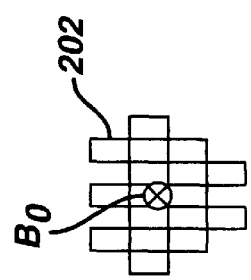
FIGS. 18c and 18d illustrate single line and multiline beam steering from a 2D transducer array patch.
Figure 18D:
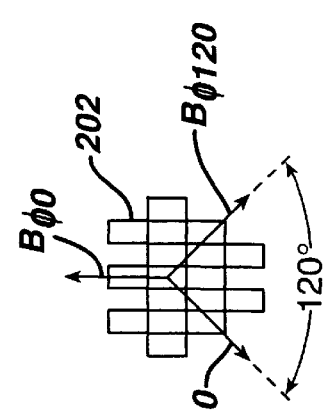

FIG. 18c illustrates a single scanline $B_0$ oriented normal to the patch 202, as would be produced by the system shown in FIG. 18a, which has a beam nominally steered normal to the face of the patch 202.

Although the foregoing examples suggest the use of a rectangular scan geometry for a rectilinear array and a triangular scan geometry for a hexagonal array, the scan geometry is not intrinsically linked to array geometry. A rectangular scan can be performed using a hexagonal array and vice versa.

A system operating as illustrated by FIG. 18d is shown in FIG. 18b. The scanhead in this drawing includes a 12 element patch micro-beamformer which produces three multiline signals from each patch ($B_{\phi 0}$, $B_{\phi 120}$ and $B_{\phi 240}$, for example) instead of one line as did the micro-beamformer 280 of FIG. 18a. The micro-beamformed patch multilines are sent over the n conductors of a cable 351 to the ultrasound system's multiline beamformer 352. The multiline scanlines from all of the patches are combined in the system multiline beamformer 352 to form multiple scanlines. It is also possible to perform r.f. interpolation between the multiline scanlines. However, rather than combine (beamform) the multiline signals from each patch and then perform r.f. interpolation on the beamformed signals, it is preferred that r.f. interpolation is performed on signals received from each patch separately prior to beamforming combination. In this case, prior to the weighting and summation operations of r.f. interpolation, each patch signal for each nominal steering direction is slightly delayed or advanced by an amount determined by each patch position and the offset of the interpolated line from the nominal line. The effect of the delays is to maximize the coherence of the patch waveforms combined in the r.f. interpolation step. This reduces interpolation errors and improves sensitivity. Specifically, if N interpolated lines are produced from M patches, each patch having K multilines, then MN r.f. interpolators are required with each interpolator preceded by K delay states, one for each multiline. This same approach (i.e., delay+individual patch r.f. interpolation prior to patch signal combination) can also be used on patch signals received from different directions in a non-multiline mode provided that target motion between successive transmits is not excessive. The multiple scanlines are then processed by the image processor 284 and displayed on the display 100 as described previously. The number n of receive signal conductors of the cable is 768 if three multilines from each of 256 patches are sent simultaneously without multiplexing, a number which can be reduced by multiplexing if desired. The patch multilines received by the ultrasound system can be interpolated to form additional scanlines prior to system beamformation if desired. However, since the processing of interpolation (weighting and summing) is mathematically compatible with that of beamformation, the patch multilines can be supplied directly to the system beamformer for formation of beamformed multilines.

Figure 20:
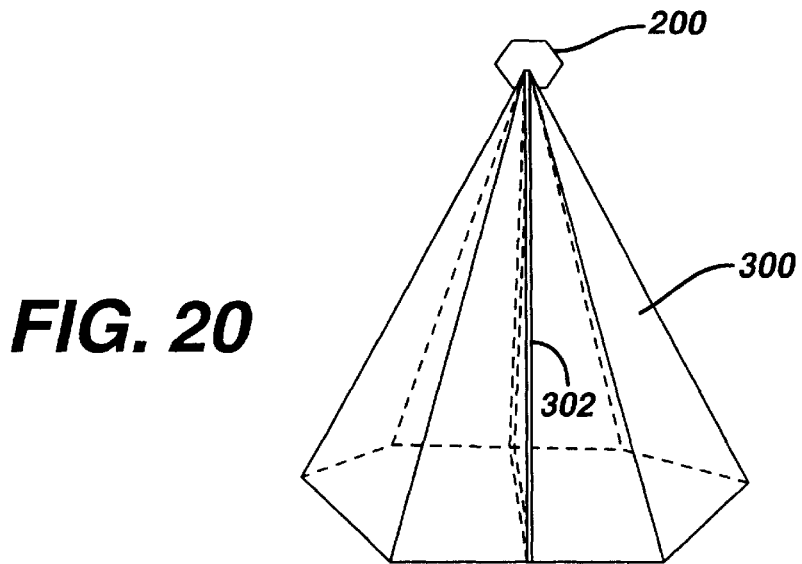
FIG. 20 illustrates a three dimensional volume containing a two dimensional image plane.
Figure 21:
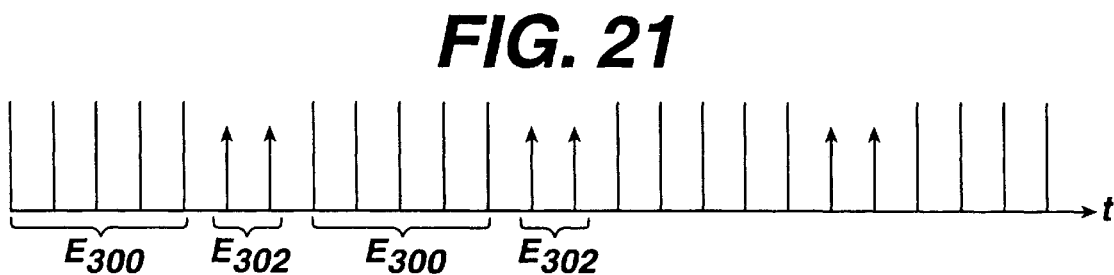
FIG. 21 illustrates the time interleaved sampling of the three dimensional volume and two dimensional image plane of FIG. 20.

Several display formats may be used for the three dimensional display of the present invention. FIG. 20 shows a volumetric region 300 which is being scanned by a 2D transducer array 200. The volumetric region scanned can be in any desired shape, such as square, cylindrical, or pyramidal, depending upon the steering of the beams from the transducer. In this example the volumetric region 300 is shown as a hexagonal pyramid. Shown within the volumetric region 300 is an image plane 302, which is delineated by the double lines. The image plane 302 is scanned in a time interleaved manner as the volumetric region 300 is scanned. The time interleaving enables the echo data from the image plane 302 to be fully acquired in less time than that required to scan the full volumetric region 300 and the frame rate of display of the image plane 302 is thus greater than that of the volumetric display. The time interleaving of the volumetric and planar image data is illustrated by FIG. 21. This drawing shows a sequence $E_{300}$ during which echo data is acquired for the volumetric display. This sequence is periodically interrupted during which echo data $E_{302}$ for the planar display is acquired. Some of the planar echo data can be used for both displays. The relative durations of the sequences and the number of transmit-receive cycles needed for each display determine the frame rate relationship of the two displays.

Figure 22:
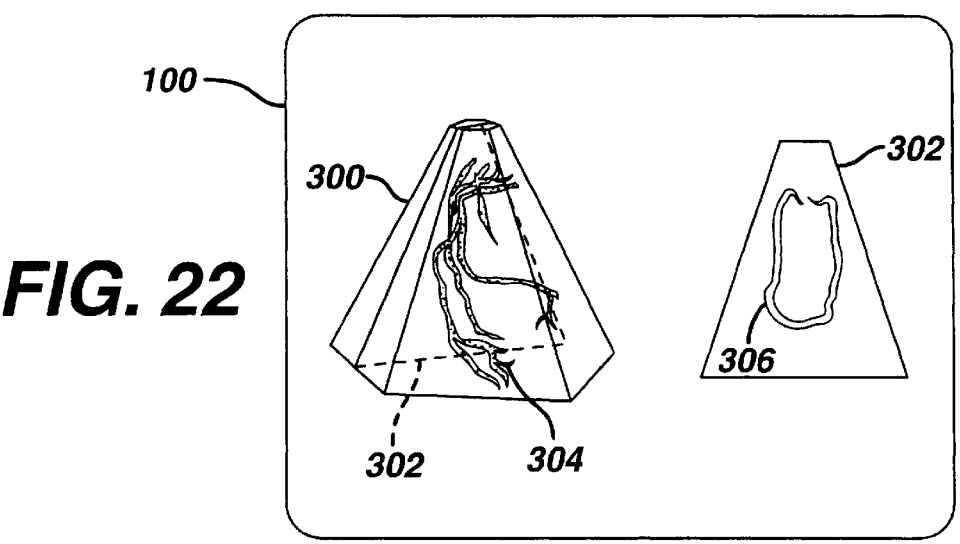
FIG. 22 illustrates a duplex display of the three dimensional volume and two dimensional image plane of FIG. 20.

The volumetric and the planar images are preferably displayed together as illustrated in FIG. 22. On the left side of the display 100 is a three dimensional display of the volumetric region 300, which shows the structure 304 in the volumetric region in a three dimensional presentation. On the right side of the display 100 is the two dimensional image plane 302, effectively showing a cut plane 306 through the three dimensional structure 304. While the frame rate of display of the three dimensional image 300 may be relatively low, the frame rate of display of the two dimensional image 302 will be much higher, which is useful when diagnosing moving objects such as the heart. Preferably the location of the two dimensional plane 304 will be indicated in the three dimensional display, as shown in this example. This gives the user a basis of reference for the two dimensional image plane within the volumetric region. The user has the ability to move the location of the cut plane 306 within the volumetric region so that a selected pathology can be viewed at the higher frame rate. By manipulating a pointing device such as a mouse or trackball the position of the image plane 302 within the volumetric region 300 can be changed on the left side of the display. The user is given a choice of rotating the cut plane about the center axis of the volumetric region, or of dragging or moving the cut plane to an arbitrarily chosen position within the volume. Thus, the display 100 displays a volumetric region at a relatively low frame rate, and a selected plane at a higher realtime frame rate. This method applies when the cut plane extends from the transducer aperture, that is, the cut plane is not a "c" plane.

Figure 23:
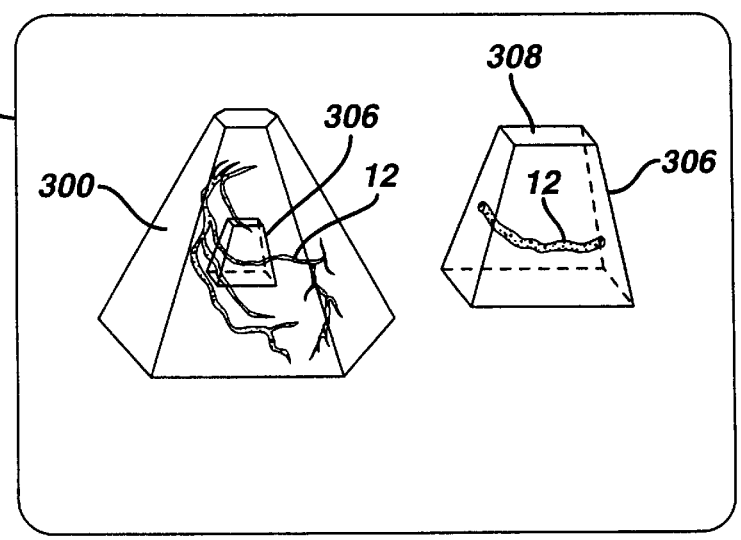
FIG. 23 illustrates a duplex display of a large three dimensional volume and a smaller three dimensional volume contained within the larger volume.

Another useful time interleaved display format is shown in FIG. 23. Instead of interrupting scanning of the volumetric region 300 to scan an image plane, the scanning of the full volumetric region is interrupted to scan a smaller volume 306 within the volumetric region 300 for a higher frame rate of display of the smaller volume. The scanning sequence is. therefore $E_{300}$, $E_{306}$, $E_{300}$, $E_{306}$, $E_{300}$, and so forth. FIG. 23 shows the display of the full volumetric region 300. Outlined within the volumetric region 300 is the smaller volumetric region 306. The smaller volume region is shown in an enlarged view at the right side of the display. Since the smaller volume 306 is fully scanned more frequently than the full volumetric region 300, the frame rate of display of the smaller volume is greater than that of the full volumetric region. The number of beams and hence the time required to scan the smaller volume is a function of the lateral dimensions of the smaller volume, the plane of FIG. 19, which in this example are the dimensions of top 308 and bottom areas of the smaller volume. Thus the frame rate of display of the smaller volume, and of both volumetric displays, can be increased by reducing the size of the top 308 of the smaller volume. As in the previous example, the user may have the choice of rotating the smaller volume about a center line within the volumetric region or relocating the smaller volume to a desired arbitrary location within the volumetric region 300. In this example the user has positioned the smaller volume to encompass a portion of a coronary artery 12 which is to be closely diagnosed for signs of obstruction, which may be more confidently done in the enlarged, higher frame rate smaller volume image 306. Such a diagnosis would preferably be done using a Doppler mode, and preferably the power Doppler mode with surrounding tissue rendered highly transparent or completely eliminated.

Figure 24:
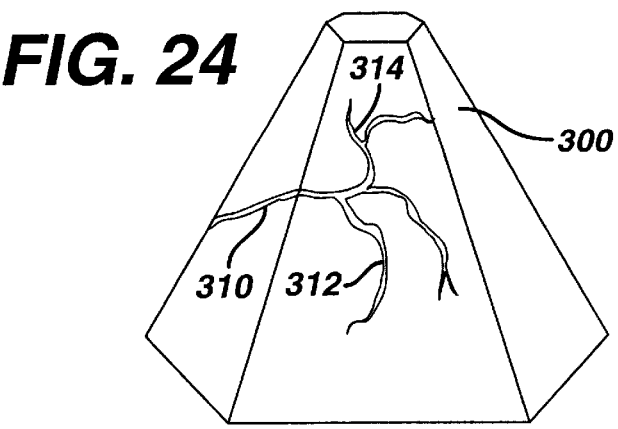
FIG. 24 illustrates a three dimension image volume containing coronary arteries.
Figure 25:
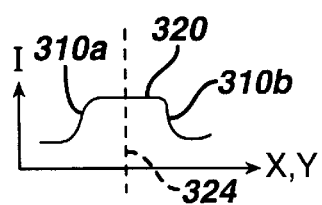
FIG. 25 illustrates an algorithm for detecting the center of a blood vessel in a three dimensional image.
Figure 26:
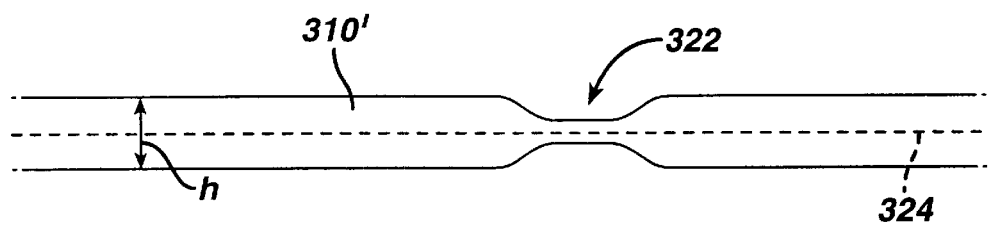
FIG. 26 illustrates a "straightened" display of one of the coronary arteries of FIG. 23.

FIGS. 24–26 illustrate another display format which is useful for coronary artery imaging as well as other vasculature. FIG. 24 illustrates a volumetric region 300 which includes a three dimensional image of coronary arteries. A main artery 310 extends from the left side of the volume and subdivides into branches 312 and 314. As shown and described above, the coronary arteries follow twisting, tortuous paths as they traverse the surface of the heart. A more confident diagnosis could be obtained if these arteries could be effectively "straightened out" for diagnosis. FIGS. 25 and 26 illustrate a technique for doing so. The clinician denotes a particular vessel for diagnosis, such as artery 310. The ultrasound system them automatically traces the designated vessel. One way to do so is illustrated in FIG. 25, in which the abscissa is the spatial dimension of the ultrasound image and the ordinate is the intensity or brightness of the image. The curve 320 illustrates the change in color or brightness across artery 310 from one side of the vessel to the other. For example, the vessel may be colored red against a gray background. The color red would increase as one side of the vessel is encountered and the curve 320 rises at 310a, and decreases at the other side of the vessel at the downslope 310b of the curve 320. From slopes 310a and 310b the ultrasound system can readily determine the center 324 of the artery and can therefore trace along the center of the vessel in the image. If the automatic trace incorrectly branches, such as following branch 312 when the clinician would like the trace to follow branch 314, the clinician can click on branch 312 to erase its trace and click on branch 314 to continue the trace of artery 310 onto branch 314.

Once the desired vessel path is identified, the vessel path is redisplayed in a straight path along its centerline 324 as shown in FIG. 26. The vessel can be displayed in a cross-sectional view along the centerline if desired or, since the vessel is in three dimensions in the image of FIG. 24, the vessel can be "unwrapped" and the outer circumference displayed. as the image height h in FIG. 26. When the vessel is shown in this "straightened" display and enlarged as desired, obstructions in the flow path such as that shown at 322 can be more readily identified. Obstructions can often be more readily observed in an "unwrapped" display of the vessel circumference.

What is claimed is:

1. A method for ultrasonically scanning a volumetric region by means of a scanhead including a two dimensional array of transducer elements coupled to an ultrasonic imaging system comprising:

acquiring a plurality of scanlines from the volumetric region comprising at least a portion of a scanline pattern which, when viewed axially along the scanlines, is hexagonal in shape; and interpolating two or more of the plurality of scanlines to increase the scanline density of the hexagonal pattern.

2. The method of claim 1, wherein acquiring comprises acquiring at least six scanlines which, when viewed axially, form a hexagon.

3. The method of claim 2, wherein acquiring comprises acquiring the six scanlines simultaneously by multiline acquisition.

4. The method of claim 3, wherein acquiring comprises acquiring the six scanlines from locations insonified by a single transmit beam.

5. The method of claim 1, wherein interpolating further comprises linearly interpolating a scanline spatially located between two or more scanlines acquired during acquiring.

6. The method of claim 5, wherein interpolating further comprises performing two-point interpolation of two spatially distinct scanlines.

7. The method of claim 6, wherein interpolating further comprises weighting the values of spatially distinct scanlines by weighting factors which are a factor off two ($2^{-1}$).

8. The method of claim 7, wherein interpolating further comprises utilizing weighting factors which are in the proportions of ¼:¾.

9. The method of claim 5, wherein interpolating further comprises linearly interpolating a scanline spatially located between two interpolated scanlines.

10. The method of claim 1, wherein interpolating further comprises performing r.f. interpolation of scanline data.

11. The method of claim 1, further comprising filtering interpolated scanline data.

12. An ultrasonic diagnostic imaging system for three dimensional imaging comprising:

a scanhead including a two dimensional array of transducer elements which transmits beams of ultrasonic energy into a volumetric region and receives ultrasound signals in return;

a beamformer coupled to the elements of the array which acts to form scanlines from the volumetric region in at least part of a hexagonal pattern; and an interpolator coupled to the beamformer which forms interpolated scanlines in the hexagonal pattern.

13. The ultrasonic diagnostic imaging system of claim 12, wherein the beamformer comprises a multiline beamformer which acts to produce a plurality of scanlines in response to a single transmit event.

14. The ultrasonic diagnostic imaging system of claim 12, wherein the interpolator comprises an r.f. interpolator.

15. The ultrasonic diagnostic imaging system of claim 12, wherein the interpolator comprises a linear interpolator.

16. The ultrasonic diagnostic imaging system of claim 15, wherein the interpolator comprises an interpolator which combines weighted scanline pairs to produce an interpolated scanline.

17. The ultrasonic diagnostic imaging system of claim 16, wherein the interpolator further comprises scanline weighting values of ½, ½.

18. The ultrasonic diagnostic imaging system of claim 16, wherein the interpolator further comprises scanline weighting values of ¼, ¾.

19. The ultrasonic diagnostic imaging system of claim 12, wherein the interpolator further comprises a multi-level interpolator which forms interpolated scanlines from other interpolated scanlines.

20. The ultrasonic diagnostic imaging system of claim 12, further comprising a filter, coupled to the interpolator, which acts to filter interpolated scanline data.

* * * * *

UNITED STATES PATENT AND TRADEMARK OFFICE
CERTIFICATE OF CORRECTION

PATENT NO.     : 6,471,650 B2
DATED          : October 29, 2002
INVENTOR(S)    : John D. Fraser, Clifford R. Cooley and Brent Stephen Robinson It is certified that error appears in the above-identified patent and that said Letters Patent is hereby corrected as shown below:

<u>Title page,</u>
Item [75], Inventors should read:
-- [75] Inventors:  John D. Fraser, Woodinville; Clifford R. Cooley, Seattle; Brent Stephen Robinson, Kirkland, all of Washington --

Signed and Sealed this

Eighteenth Day of March, 2003

JAMES E. ROGAN
*Director of the United States Patent and Trademark Office*